United States Patent
Kalluri

(10) Patent No.: US 8,592,166 B2
(45) Date of Patent: Nov. 26, 2013

(54) HYPOXIA RELATED GENES AND PROTEINS FOR THE TREATMENT AND DIAGNOSIS OF PREGNANCY RELATED COMPLICATIONS

(75) Inventor: Raghu Kalluri, Weston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 827 days.

(21) Appl. No.: 12/515,594

(22) PCT Filed: Nov. 21, 2007

(86) PCT No.: PCT/US2007/085355
§ 371 (c)(1),
(2), (4) Date: Feb. 23, 2010

(87) PCT Pub. No.: WO2008/103202
PCT Pub. Date: Aug. 28, 2008

(65) Prior Publication Data
US 2010/0178283 A1    Jul. 15, 2010

Related U.S. Application Data

(60) Provisional application No. 60/860,331, filed on Nov. 21, 2006.

(51) Int. Cl.
*G01N 33/53* (2006.01)
*G01N 33/541* (2006.01)
*A61K 38/45* (2006.01)

(52) U.S. Cl.
USPC ............................ 435/7.1; 435/7.92; 424/94.5

(58) Field of Classification Search
USPC .................................. 435/7.1, 7.92; 424/94.5
See application file for complete search history.

(56) References Cited

U.S. PATENT DOCUMENTS

| | | |
|---|---|---|
| 4,963,590 A | 10/1990 | Backstrom et al. |
| 5,643,900 A | 7/1997 | Fotsis et al. |
| 5,739,302 A | 4/1998 | Suzuki et al. |
| 7,407,659 B2 | 8/2008 | Karumanchi et al. |
| 2002/0082433 A1 | 6/2002 | Agoston et al. |
| 2002/0147183 A1 | 10/2002 | Agoston et al. |
| 2004/0126828 A1* | 7/2004 | Karumanchi et al. ....... 435/7.92 |
| 2006/0172943 A1 | 8/2006 | Edelberg et al. |
| 2008/0160105 A1 | 7/2008 | Folkman et al. |

FOREIGN PATENT DOCUMENTS

| | | |
|---|---|---|
| CA | 1302418 C | 6/1992 |
| EP | 0237929 B1 | 6/1993 |
| GB | 2200109 A | 7/1988 |
| WO | 96/37456 A1 | 11/1996 |
| WO | 2005/023197 A3 | 3/2005 |
| WO | 2005/110462 A3 | 11/2005 |

OTHER PUBLICATIONS

Nevo et al., "Increased expression of sFlt-1 in in vivo and in vitro models of human placental hypoxia is mediated by HIF-1," Am J Physiol Regul Integr Comp Physiol 291:R1085-R1093, Apr. 2006.*

(Continued)

*Primary Examiner* — Rosanne Kosson
(74) *Attorney, Agent, or Firm* — Mark J. FitzGerald; Shayne Y. Huff; Nixon Peabody LLP

(57) ABSTRACT

The invention features methods for diagnosing and treating pregnancy related complications. The invention also features methods for identifying compounds useful for treating pregnancy related complications.

9 Claims, 12 Drawing Sheets

(56) References Cited

OTHER PUBLICATIONS

Kono, S., et al. "Radioimmunoassay and Metabolic Clearance Rate of Catecholestrogens, 2-Hydroxyestrone and 2-Hydroxyestradiol in Man" J. Steroid Biochem., vol. 19, No. 1, 1983 pp. 627-633.

Park, J., et al., "Hypoxia-Inducible Factor 1-Related Diseases and Prospective Therapeutic Tools" J. Pharmacol Sci 94, 2004, pp. 221-232.

Sun, et al., "Associateion between catechol-methyltransferase gene polymorphism and pregnancy induced hypertension" Database Medline [Online] US National Library of Medicine (NLM), Bethesda, MD, US, Accession No. NLM14989982, Abstract. XP-002568262, Jan. 1, 2004.

Acien, P. et al., "Perinatal morbidity and mortality in pregnancy hypertensive disorders: prognostic value of the clinical laboratory findings," International Journal of Gynecology and Obstetrics, 32(3):229-235 (1990).

Ahmad, S. et al., "Elevated placental soluble vascular endothelial growth factor receptor-1 inhibits angiogenesis in preeclampsia," Circ. Res. 95:884-891 (2004).

Barnea, E.R. et al. "Catechol-O-methyltransferase activity in the human term placenta," American Journal of Perinatology, Thieme-Stratton, New York, NY, US 5(2):121-127 (1988).

Bates, G.W. et al., "Erythrocyte catechol-O-methyltransferase activity in pregnant women with prenancy-induced hypertension", American Journal of Obstetrics & Gynecology, Mosby, St. Louis, MO, US 142(2):177-178 (1982).

Bennedsen, B.E. et al., "Obstetric complications in women with schizophrenia," Schizophr. Res. 47:167-175 (2001).

Bhansali, K.G. et al., "Quantitative determination of 17 beta-estradiol and progesterone in cellular fractions of term placentae of normal and hypertensive patients," Database Medline [Online], U.S. National Library of Medicine, 1992, XP002531982.

Nadar, S. et al., "Plasma markers of angiogenesis in pregnancy induced hypertension," Thromb Haemost 94:1071-1076 (2005).

Casey, M.L. et al., "Characterization of catechol-O-methyltransferase activity in human uterine decidua vera tissue," Am. J. Obstet. Gynecol. 145:453-457 (1983).

Chen, C. et al., Systematic Mutation Analysis of the Catechol O-Methyltransferase Gene as a Candidate Gene for Schizophrenia, Am. J. Psychiatry 156:1273-1275 (1999).

Chen, J. et al., "Functional Analysis of Genetic Variation in Catechol-O-Methyltransferase (COMT): Effects on mRNA, Protein, and Enzyme Activity in Postmortem Human Brain," Am. J. Hum. Genet. 75:807-821 (2004).

Cotton, N.J.H. et al., Oxidative Inhibition of Human Soluble Catechol-O-Methyltransferase, J. Biol. Chem. 279:23710-23718 (2004).

Cushman, M. et al., "Synthesis, Antitubulin and Antimitotic Activity, and Cytotoxicity of Analogs of 2-Methoxyestradiol, and Endogenous Mammalian Metabolite of Estradiol That Inhibits Tubulin Polymerization by Binding to the Colchicine Binding Site," J. Med. Chem. 38:2041-2049 (1995).

Gogos, J.A. et al., "Catechol-O-methyltransferase-deficient mice exhibit sexually dimorphic changes in catecholamine levels and behavior," Proc. Natl Acad. Sci. USA 95:9991-9996 (1998).

Kanasaki, K. et al., "Deficiency in catechol-O-methyltransferase and 2-methoxyoestradiol is associated with pre-eclampsia, Nature," 453:1117-1123 (2008).

Kendell, R.E., "Obstetric Complications and Schizophrenia: A Case Control Study Based on Standardized Obstetric Records," British J. Psychiatry 168:556-561 (1996).

Khong, T.Y. et al., "Inadequate Maternal Vascular Response to Placentation in Pregnancies Complicated by Pre-Eclampsia and by Small-for-Gestational Age Infants," Britsh J. Obstet. Gynecol., 93:1049-1059 (1986).

Kirov, G. et al., Low Activity Allele of Catechol-O-Methyltransferase Gene Associated with Rapid Cycling Bipolar DisorderMol. Psychiatry 3:342-345 (1998).

Levine, R.J. et al., "Circulating angiogenic factors and the risk of preeclampsia," N. Engl. J. Med. 350:672-683 (2004).

Lindheimer, M.D. et al., "Annual Review of Medicine," 40:233-250 (1989).

Luttun, A. et al., "Soluble VEGF Receptor Flt1: the elusive preeclampsia factor discovered?" Journal of Clinical Investigation 111:600-602 (2003).

Maynard, S.E. et al. "Excess placental soluble fms-like tyrosine kinase 1 (sFlt1) may contribute to endothelial dysfunction, hypertension, and proteinuria in preeclampsia," J. Clin. Invest. 111:649-658 (2003).

McCoy, S. et al., "Pharmacotherapeutic options for the treatment of preeclampsia," Am. J. Health-Syst. Pharm. 66:337-344 (2009).

Mizutani, S. et al., "Positive effect of estradiol and progesterone in severe preeclampsia," Experimental and Clinical Endocrinology 92(2):161-170 (1988).

Mooberry, S.L., "Mechanism of action of 2-methoxyestradiol: new developments," Drug Resistance Updates: Review and Commentaries in Antimicrobial and anticancer Chemotherapy, 6(6):355-361 (2003).

Nadar, S. et al., "Plasma markers of angiogenesis in pregnancy induced hypertension," American Journal of Hypertension, 17(5) Part 2:161A-162A (2004).

Nagamatsu, T. et al. "Cytotrophoblasts up-regulate soluble fms-like tyrosine kinase-1 expression under reduced oxygen: an implication for the placental vascular development and the pathophysiology of preeclampsia," Endocrinology 145(11):4838-4845 (2004).

Redman, C.W. et al., "Latest advances in understanding preeclampsia." Science 308:1592-1594 (2005).

Roberts, J.M. et al., "Clinical and Biochemical Evidence of Endothelial Cell Dysfunction in the Pregnancy Syndrome Preeclampsia," Am. J. Hypertens. 4:700-708 (1991).

Robertson, W.B. et al., "The Placental Bed Biopsy: Review from Three European Centers," Am J. Obstet. Gynecol., 155(2):401-412 (1986).

Sata, F. et al., "Functional maternal catechol-O-methyltransferase polymorphism and fetal growth restriction," Pharmacogenet. Genomics 16:775-781 (2006).

Sugimoto, H. et al., "Neutralization of circulating vascular endothelial growth factor (VEGF) by anti-VEGF antibodies and soluble VEGF receptor 1 (sFlt-1) induces proteinuria," J. Biol. Chem. 278:12605-12608 (2003).

Sun et al, "Association between catechol-methyltransferase gene polymorphism and pregnancy induced hypertension", Database Medline [Online] US National Library of Medicine (NLM), Bethesda, MD, US, Accession No. NLM14989982, Abstract. XP-002568262.

Svedas, E. et al., Endothelial dysfunction in uterine circulation in preeclampsia: Can estrogens improve it? American Journal of Obstetrics and Gynecology, 187(6):1608-1616 (2002).

Takanashi K. et al., On the Inhibitory Effect of C17-Sulfoconjugated Catechol Estrogens upon Lipid Peroxidation of Rat Liver Mircrosomes, Biol. Pharm. Bull. 18(8):1120-1125 (1995).

Takanashi, K. et al., "Detection and measurement of urinary 2-hydroxyestradiol 17-sulfate a potential placental antioxidant during pregnancy," Clin. Chem. 46(3):373-378 (2000).

Takanashi, K. et al., "Comparison of ex vivo Inhibitory Effect Between 2-Hydroxyestradiol and Its 17-Sulfate on Rat Hepatic Microsomal Lipid Peroxidation," Lipids 38(8):847-854 (2003).

Takanashi, K., "Studies on 2-hydroxyestradiol 17-sulfate derived from fetoplacental unit: the antioxidant as a potential defense substance against preeclampsia," Database Medline [Online], U.S. National Library of Medicine, 2003, XP002531983, Abstract only.

Tempfer, C. et al. "Applications of polymorphisms and pharmacogenomics in obstetrics and gynecology," Pharmacogenomics, Ashley Publications, GB, 5(1):57-65 (2004).

Tofovic et al., "Estradiol Metabolites Attenuate Renal and Cardiovascular Injury Induced by Chronic Angiotensin 11 Administration," Journal of the American Society of Nephrology 14:620A, SU-PO394 (2003). Abstract.

Tron et al., "Miniperspective, Medicinal Chemistry of Combretastatin A4: Present and Future Directions," J. Med. Chem. 49(11):3033-3044 (2006).

(56) References Cited

OTHER PUBLICATIONS

Vuorela, P. et al., "Amniotic fluid-soluble vascular endothelial growth factor receptor-1 in preeclampsia," Obstet. Gynecol. 95:353-357 (2000).

Wonodi, I. et al., "Association Between Val 108/158 Met Polymorphism of the COMT Gene and Schizophrenia," Am. J. Med. Genet. 120B:47-50 (2003).

Xie et al., "Characterization and Implications of Estrogenic Down-Regulation of Human Catechol-O-Methyltransferase Gene Transcription," Molecular Pharmacology 56(31):31-38 (1999).

Zeisler, H. et al., "Concentrations of estrogens in patients with preeclampsia," Wiener Klinische Wochenschrift, 114 (12):458-461 (2002).

Pribluda et al., 2-Methoxyestradiol: An endogenous antiangiogenic and antiproliferative drug candidate, Cancer and Metastasis Reviews 19: 173-179 (2000).

Rumbold et al., Antioxidants for preventing pre-eclampsia, Cochrane Database of Systematic Reviews 2008, Issue 1, Art. No. CD004227. DOI: 10.1002/14651858.CD004227.pub3.: 1-83 (2008).

Rutland et al., Induction of Intrauterine Growth Restirciton by Reducing Placental Vascular Growth with the Angioinhibin TNP-470, Biology of Reproduction 73, 1164-1173 (2005).

* cited by examiner

Fig. 4 Experimental protocol

Fig. 6 Maternal-Fetal Interface

Fig. 9 Blood pressure (COMT KO)

Fig. 11 Urinary Albumin Excretion

Fig. 12

Administration of 2ME (5 mgs/day/iv) during the last 7 days of mouse gestation does not lead to pregnancy complications, altered litter size or abnormal development

| Mice/Strain | Control/Vehicle | 2ME in PBS (5 mgs/ml) |
|---|---|---|
| C57Bl/6 | 46+/-9 | 52+/-12 |
| 129/sv | 61+/-8 | 57+/-6 |
| CD-1 | 67+/-11 | 63+/-7 |

7 litters

HYPOXIA RELATED GENES AND PROTEINS FOR THE TREATMENT AND DIAGNOSIS OF PREGNANCY RELATED COMPLICATIONS

CROSS-REFERENCE TO RELATED APPLICATIONS

This application is a National Phase Entry Application Under 35 U.S.C. §371 of International Application No. PCT/US2007/85355 filed Nov. 21, 2007, which designates the United States, and which claims benefit under 35 U.S.C. §119(e) of United States Provisional Patent Application No. 60/860,331 filed Nov. 21, 2006, the contents of which are incorporated herein by reference in their entirety.

FIELD OF THE INVENTION

In general, this invention relates to the detection and treatment of subjects having pre-eclampsia or eclampsia.

BACKGROUND OF THE INVENTION

Pre-eclampsia is a syndrome of hypertension, edema, and proteinuria that affects 5 to 10% of pregnancies and results in substantial maternal and fetal morbidity and mortality. Pre-eclampsia accounts for at least 200,000 maternal deaths worldwide per year. The symptoms of pre-eclampsia typically appear after the $20^{th}$ week of pregnancy and are usually detected by routine measuring of the woman's blood pressure and urine. However, these monitoring methods are ineffective for diagnosis of the syndrome at an early stage, which could reduce the risk to the subject or developing fetus, if an effective treatment were available.

Currently there are no known cures for pre-eclampsia. Pre-eclampsia can vary in severity from mild to life threatening. A mild form of pre-eclampsia can be treated with bed rest and frequent monitoring. For moderate to severe cases, hospitalization is recommended and blood pressure medication or anticonvulsant medications to prevent seizures are prescribed. If the condition becomes life threatening to the mother or the baby the pregnancy is terminated and the baby is delivered pre-term.

The only known treatments for pre-eclampsia include antihypertensive therapy or delivery of the baby, which may jeopardize the health of the baby, the mother, or both.

The hallmarks of pre-eclampsia include hypertension, proteinuria, and edema. Placental maladaptation and body-wide endothelial cell dysfunction underlie these clinical manifestations. Failure of trophoblastic invasion into myometrial segments of maternal spiral arteries and the production of cytotoxic mediators which cause systemic endothelial damage also seem to be implicated. During normal development human trophoblasts invade through the extracellular matrix into the myometrial portion of spiral arteries and convert them into uteroplacental arteries. Uteroplacental arteries then dilate approximately 30-fold as large as the spiral arteries. The resulting hemodynamic changes enable the placental bed to satisfy the increased demand for oxygen from the fetus during the latter stages of gestation. In pre-eclamptic women, however, spiral arteries are not properly converted into uteroplacental arteries due to the failure of the second wave of trophoblastic migration into the myometrium at the beginning of the second trimester. As a result, pre-eclamptic women typically demonstrate a high-resistance, high-pressure, and low-flow state with intact, non-dilated spiral arteries, and demonstrate a wide variety of clinical syndromes.

Hypoxia refers to a condition in which the oxygen level is reduced below the normal physiological range. Hypoxic conditions have been shown to lead to increased sFlt-b 1 production by placental trophoblasts. sFlt-1 is a soluble form of the Flt-1 receptor, which is a receptor for VEGF and PlGF. Increases in sFlt-1 have been shown to be associated with pre-eclampsia, as have decreases in free VEGF and PlGF. Elevated levels of the soluble focus of the receptor can then bind to free VEGF and PlGF resulting in a decrease in the levels of these proteins. This imbalance in the levels and activity of these and other proteins is thought to be one of the contributing factors of pre-eclampsia or eclampsia.

All of the factors that contribute to the proper development of the fetus and the placenta have not yet been identified. There remains a need for the identification of the factors that are improperly regulated during pre-eclampsia and eclampsia. With such knowledge, methods of accurately diagnosing subjects at risk for or having pre-eclampsia or eclampsia, can be developed as well as therapeutic methods for the treatment and prevention of pre-eclampsia. It is therefore an object of the present invention to overcome these shortcomings in existing treatments for pre-eclampsia by providing safe and effective methods and compositions for the treatment of pre-eclampsia and other pregnancy related disorders.

SUMMARY OF THE INVENTION

We have discovered methods for diagnosing and treating pregnancy related hypertensive disorders, including gestational hypertension, pre-eclampsia, and eclampsia.

Although the causes of gestational hypertension, pre-eclampsia, and eclampsia have not yet been clearly defined, each of these conditions is characterized by some level of hypertension, proteinuria, and edema. These conditions are also characterized by a lack of oxygen to the placenta, also known as placental hypoxia, which can significantly harm the developing fetus and can jeopardize the health of the mother.

We have discovered that several of the proteins and small molecule compounds that regulate the hypoxia pathways, for example 2-methoxyestradiol (2-ME) and catechol-o-methyltransferase (COMT), are not expressed or functioning at normal physiological levels in women having pre-eclampsia and eclampsia. In pre-eclampsia, trophoblast cells, which, under normal conditions, invade the uterine wall and stimulate an increase in vascularity necessary to support the placenta during pregnancy, are unable to stimulate an increase in vascularity and as a result, the placenta becomes ischemic and/or hypoxic. Our proposed model is that the deficiency of these upstream factors results in placental hypoxia, which then results in alterations in the levels of angiogenic factors such as sFlt-1, VEGF, and PlGF. We have discovered that diagnostic tests for the detection of hypoxia-related proteins, nucleic acids, or small molecules can be used to diagnose pregnancy related hypertensive disorders, including gestational hypertension, pre-eclampsia or eclampsia. Furthermore, based on our discovery of the deficiencies in the hypoxia factors, the present invention features the use of the hypoxia-related proteins, nucleic acids, small molecules or analogs thereof, for the treatment or prevention of pregnancy related hypertensive disorders, including gestational hypertension, pre-eclampsia, or eclampsia. Such treatment methods can be used to prevent the hypoxic state from occurring which could, according to our model. We have also discovered that inhibitors or COMT can be used to establish a mouse model of gestational hypertension, pre-eclampsia or eclampsia, which can then be used to screen additional therapeutics for the treatment of pregnancy related hypertensive disorders.

Accordingly, in one aspect, the invention features a method of diagnosing a subject as having, or having a propensity to develop, a pregnancy related hypertensive disorder (e.g., pre-eclampsia or eclampsia). This method includes measuring the biological activity or expression level (e.g., mRNA expression level or protein expression level) of at least one polypeptide selected from the group consisting of: COMT, HIF-1α, free VEGF, total VEGF, sFlt-1, PlGF, EPO, LDH-A, ET-1, transferrin, transferrin receptor, and Flk-1, in a sample, where an alteration in the biological activity or expression level of the polypeptide or polypeptides, as compared to the biological activity or expression level in a reference sample (e.g., a sample previously taken from the subject), is a diagnostic indicator of a pregnancy related hypertensive disorder or a propensity to develop a pregnancy related hypertensive disorder. In this aspect, if the biological activity or expression level of free VEGF, total VEGF, sFlt-1, or PlGF is measured, then the biological activity or expression level of at least one of COMT, HIF-1α, EPO, LDH-A, ET-1, transferrin, transferrin receptor, and Flk-1 is also measured.

In the forgoing aspect, the alteration of the expression level or biological activity of a gene selected from the group consisting of HIF-1α, free VEGF, total VEGF, sFlt-1, PlGF, EPO, LDH-A, ET-1, transferrin, transferrin receptor, and Flk-1 can be an increase in expression level or biological activity (e.g., a 10%, 25%, 40%, 50%, 60%, 70%, 80%, 90%, or greater increase). For example, in the case of HIF-1α, the alteration can be an increase in HIF-1 α expression level or biological activity in the case of total VEGF, the alteration can be an increase in total VEGF expression level or biological activity; and in the case of sFlt-1, the alteration can be an increase in sFlt-1 expression level or biological activity.

In any of the forgoing aspects, the alteration of the expression level or biological activity of a gene selected from the group consisting of COMT, HIF-1α, free VEGF, total VEGF, sFlt-1, PlGF, EPO, LDH-A, ET-1, transferrin, transferrin receptor, and Flk-1 can be a decrease in expression level or biological activity (e.g., a 10%, 25%, 40%, 50%, 60%, 70%, 80%, 90%, or greater decrease). For example, in the case of COMT, the alteration can be a decrease in COMT expression level or biological activity, and in the case of free VEGF, the alteration can be a decrease in free VEGF expression level or biological activity.

In any of the forgoing aspects, the expression level can be measured using an immunological assay (e.g., ELISA).

In another aspect, the invention features a method of diagnosing a subject (e.g., a pregnant human, postpartum human, or non-pregnant human) as having, or having a propensity to develop, a pregnancy related hypertensive disorder (e.g., pre-eclampsia or eclampsia). This method includes determining the nucleic acid sequence of a gene encoding a polypeptide selected from the group consisting of COMT, HIF-1α, EPO, LDH-A, ET-1, transferrin, transferrin receptor, and Flk-1, in a sample, where an alteration in the subject's nucleic acid sequence that is an alteration that changes the expression level or biological activity of the gene product in the subject diagnoses the subject with a pregnancy related hypertensive disorder, or a propensity to develop a pregnancy related hypertensive disorder. In this aspect, if nucleic acid sequence of a gene encoding a polypeptide selected from the group consisting of free VEGF, total VEGF, sFlt-1, or PlGF is determined, then the nucleic acid sequence of a gene encoding a polypeptide selected from the group consisting of COMT, HIF-1α, EPO, LDH-A, ET-1, transferrin, transferrin receptor, and Flk-1 is also determined. In this aspect of the invention, the alteration can result in a decrease in the expression level or biological activity of COMT.

In another aspect, the invention features a method of treating or preventing a pregnancy related hypertensive disorder (e.g., pre-eclampsia or eclampsia) in a subject in need thereof. This method includes administering to the subject an expression vector encoding COMT, or a biologically active fragment thereof, wherein COMT is positioned in the vector for expression (e.g., under the control of a placental promoter).

In yet another aspect, the invention features a method of treating or preventing a pregnancy related hypertensive disorder (e.g., pre-eclampsia or eclampsia) in a subject in need thereof, by administering to the subject an isolated COMT protein or biologically active fragment thereof The administering can result in the treatment or prevention of at least one symptom associated with a pregnancy related hypertensive disorder (e.g., pre-eclampsia or eclampsia). These methods can also include the step of monitoring the subject after the administration of the expression vector or isolated COMT protein.

In any of the forgoing aspects, the subject of administration or diagnosis can be a pregnant or non-pregnant human (e.g., a human in the first, second, or third trimester of pregnancy, or postpartum human).

In another aspect, the invention features a method of identifying a therapeutic compound for treating a pregnancy related hypertensive disorder (e.g., pre-eclampsia or eclampsia). This method includes the steps of assaying a candidate therapeutic compound for increasing the biological activity of COMT. In this aspect, an increase is indicative of the therapeutic efficacy for treating a pregnancy related hypertensive disorder with the candidate compound. In this aspect, the assaying can include contacting the candidate therapeutic compound with COMT in vitro and measuring the biological activity of COMT. The assaying can also include contacting the therapeutic compound with a cell capable of transcribing the mRNA encoding COMT and measuring the level of expression of the mRNA.

In another aspect, the invention features a method for identifying a therapeutic compound for treating a pregnancy related hypertensive disorder (e.g., pre-eclampsia or eclampsia). This method includes inducing at least one symptom associated with a pregnancy related hypertensive disorder in a pregnant mouse by administering a compound to the mouse, where the compound decreases the expression level or biological activity of COMT. Then treating the pregnant mouse with a second compound, and determining whether the symptom of a pregnancy related hypertensive disorder is decreased by said second compound. In this method, a decrease in said symptom in the treated pregnant mouse, as compared to an untreated pregnant mouse, is indicative of the therapeutic efficacy for treating the pregnancy related hypertensive disorder with the candidate compound. In this method, the compound can be a chemical inhibitor of COMT (e.g., tolcapone, entacapone, and nitecapone).

In another aspect, the invention features a method for identifying a therapeutic compound for treating a pregnancy related hypertensive disorder (e.g., pre-eclampsia or eclampsia). This method includes treating a pregnant mouse with a compound. The pregnant mouse contains a mutation resulting in decreased COMT biological activity resulting in the induction of at least one symptom of a pregnancy related hypertensive disorder in the pregnant mouse. The method further includes determining whether the symptom of pre-eclampsia or eclampsia is decreased by the compound. A decrease in at least one symptom in the treated pregnant mouse, as compared to an untreated pregnant mouse, is indicative of the therapeutic efficacy for treating the pregnancy related hypertensive disorder with the candidate compound. In this example, the pregnant mouse can have a mutation in the COMT gene.

For the purpose of the present invention, the following abbreviations and terms are defined below.

By "alteration" is meant a change (increase or decrease). An alteration can include a change in the expression levels of a gene or polypeptide as detected by standard art known methods such as those described below. As used herein, an alteration includes a 10% change in expression levels, preferably a 25% change, more preferably a 40%, 50%, 60%, 70%, 80%, 90% or greater change in expression levels. "Alteration" can also indicate a change (increase or decrease) in the biological activity of any of the polypeptides or small molecules of the invention (e.g., COMT, HIF-1α, 2-ME, VEGF (free or total), sFlt-1, PlGF, EPO, LDH-A, ET-1, transferrin, transferrin receptor, and Flk-1). As used herein, an alteration includes a 10% change in biological activity, preferably a 25% change, more preferably a 40%, 50%, 60%, 70%, 80%, 90% or greater change in biological activity. Examples of biological activity for COMT includes enzymatic activity in the conversion of 2 hydroxyestradiol 17 sulfate to 2-methoxyestradiol (2-ME). The biological activity of COMT can be measured by assays detecting the level of 2-ME, a 2-ME metabolite, or a 2-ME precursor in the cell or using assays that measure the biological activity of 2-ME, which has an anti-angiogenic activity. Examples of such assays are described in PCT Publication No. WO2005/10462, which is hereby incorporated by reference in its entirety.

By "catechol-O-methyltransferase" or "COMT" is meant a nucleic acid or a polypeptide that is substantially identical to the nucleic acid or amino acid sequences set forth in GenBank Accession Numbers M65212 (cloned from a human placenta), M58825 (the membrane associated form), CR456997, BC005867, and BC000419, or homologs, analogs, derivatives, or fragments thereof. COMT is found in two forms in tissues, a soluble form (S-COMT) and a membrane-bound form (MB-COMT). There are also known transcript variants of COMT that are formed through the use of alternative translation initiation sites and promoters. Preferred COMT polypeptides or nucleic acid molecules encoding a COMT polypeptides will have COMT biological activity. COMT biological activity includes the conversion of 2-hydroxyestradiol 17 sulfate to 2-ME, the metabolism of endogenous catecholamine neurotransmitters, such as dopamine and noradrenaline, and exogenous catecholamines such as levodopa. Proteins with COMT activity can be identified using the assay set forth in Chen et al., Am. J. Hum. Genet. 75:807 (2004), which is hereby incorporated by reference in its entirety. Briefly, the COMT enzyme activity assay uses the organic solvent extraction method that separates the radioactive product, the methylated catechol, and the free radioactive coenzyme, $^3$H-SAM (Zurcher and Da Prada, Neurochem 38:191 (1982)). From each sample, 100 µg of human DLPFC or lymphocyte protein at a concentration of 5 µg/µl was transferred to a fresh microcentrifuge tube and equilibrated to room temperature shortly before the enzyme assay. To each tube, we added 500 µl of the substrate mixture, which contained 10 mM Tris (pH 7.4), 1 mM MgCl2, 1.5 µCi of 3H-SAM, 10 µM of catechol, and 1 µM of DTT. The tubes were then incubated at 37° C. for 20 min. The reactions were immediately terminated by the addition of 500 µl of 1M HCl. The radioisotope-labeled catechol products from the reactions were extracted by adding 10 ml of scintillation fluid to the reaction mixture and then were measured for the radioactivity of the mixture in a scintillation counter. The relative COMT enzyme activity is presented as disintegrations per minute (DPM) per mg total protein. To establish a baseline control for nonspecific reactions that do not depend on COMT, 5 µl of the specific COMT inhibitor, tolcapone (10 mg/ml), was added to a tube containing 100 µg of the human DLPFC sample. The high concentration of potent inhibitor blocked the specific reaction catalyzed by COMT, and the radioactivity from this reaction served as a baseline. Proteins with COMT activity will exhibit an activity that is greater than the baseline control.

By "substantially identical" is meant a nucleic acid or amino acid sequence that, when optimally aligned, for example using the methods described below, share at least 60%, 65%, 70%, 75%, 80%, 85%, 90%, 95%, 96%, 97%, 98%, 99%, or 100% sequence identity with a second nucleic acid or amino acid sequence, e.g., a COMT sequence. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences will be at least 10 amino acids, preferably 20, 30, 40, 50, 60, 70, 80, 90, 100, 110, 120, 130, 140, 150, 186, 200, 250, or at least 271 amino acids or more. For nucleic acids, the length of comparison sequences will generally be at least 25, 50, 100, 125, 150, 200, 250, 300, 350, 400, 450, 500, 550, 600, 650, 700, 800, or at least 813 nucleotides or more. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "compound" is meant any small molecule chemical compound, antibody, nucleic acid molecule, or polypeptide, or fragments thereof.

By "expression" is meant the detection of a gene or polypeptide by methods standard in the art. For example, polypeptide expression is often detected by western blotting, DNA expression is often detected by Southern blotting or polymerase chain reaction (PCR), and RNA expression is often detected by northern blotting, quantitative PCR, or RNAse protection assays. Methods to measure protein expression levels generally include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Any compound that increases the levels of a polypeptide, nucleic acid, or small molecule of the invention (e.g., COMT) by at least 10%, 20%, preferably 30%, more preferably at least 40% or 50%, and most preferably at least 60%, 70%, 80%, 90% or more is considered a therapeutic compound of the invention.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 813 or more nucleotides or 10, 20, 30, 40, 50, 60, 70, 80, 90, 100, 150, 186, 200, 250, 271 amino acids or more. Preferred fragments have COMT biological activity.

By "gestational age" is meant a reference to the age of the fetus, counting from the first day of the mother's last menstrual period usually referred to in at least one week.

By "gestational hypertension" is meant the development of high blood pressure without proteinuria after 20 weeks of pregnancy.

By "having or having a propensity to develop schizophrenia" is meant a patient diagnosed with schizophrenia or having a history of schizophrenia. By a "history of schizophrenia" is meant a previous diagnosis of schizophrenia in the subject themselves or in a related family member. By schizophrenia is meant a type of psychosis, characterized by a disorder in the thinking processes, such as delusions and hallucinations, and extensive withdrawal of the individual's interest from other people and the outside world, and the investment of it in his own; now considered a group of mental disorders rather than as a single entity, with distinction sometimes made between process schizophrenia and reactive schizophrenia. Symptoms of schizophrenia are varied in each patient but are well known to the skilled artisan.

By a "history of a pregnancy related hypertensive disorder" is meant a previous diagnosis of a pregnancy related hypertensive disorder (e.g., pre-eclampsia or eclampsia or gestational hypertension) in the subject themselves or in a related family member.

By "homologous" is meant any gene or protein sequence that bears at least 30% homology, more preferably 40%, 50%, 60%, 70%, 80%, and most preferably 90% or more homology to a known gene or protein sequence over the length of the comparison sequence. A "homologous" protein can also have at least one biological activity of the comparison protein. In general, for proteins, the length of comparison sequences will be at least 10 amino acids, preferably 10, 20, 30, 40, 50, 60, 70, 80, 90, 100, 150, 186, 200, 250, or at least 271 amino acids or more. For nucleic acids, the length of comparison sequences will generally be at least 25, 50, 100, 125, 150, 200, 250, 300, 350, 400, 450, 500, 550, 600, 650, 700, 800, or at least 813 nucleotides or more.

By "hybridize" is meant pair to form a double-stranded molecule between complementary polynucleotide sequences, or portions thereof, under various conditions of stringency. (See, e.g., Wahl and Berger *Methods Enzymol.* 152:399, 1987; Kimmel, *Methods Enzymol.* 152:507, 1987.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196:180, 1977); Grunstein and Hogness (*Proc. Natl. Acad. Sci.*, USA 72:3961, 1975); Ausubel et al. (*Current Protocols in Molecular Biology*, Wiley Interscience, New York, 2001); Berger and Kimmel (*Guide to Molecular Cloning Techniques*, 1987, Academic Press, New York); and Sambrook et al., *Molecular Cloning: A Laboratory Manual*, Cold Spring Harbor Laboratory Press, New York.

By "metric" is meant a measure. A metric may be used, for example, to compare the levels of a polypeptide or nucleic acid molecule of interest. Exemplary metrics include, but are not limited to, mathematical formulas or algorithms, such as ratios. The metric to be used is that which best discriminates between levels of COMT, HIF-1α, 2-ME, VEGF (free or total), sFlt-1, PlGF, EPO, LDH-A, ET-1, transferrin, transferrin receptor, Flk-1, or any combination thereof, in a subject having pregnancy related hypertensive disorder, such as pre-eclampsia or eclampsia, and a normal control subject. Depending on the metric that is used the diagnostic indicator of pregnancy related hypertensive disorder may be significantly above or below a reference value (e.g., from a control subject not having a pregnancy related hypertensive disorder or from a previous sample taken prior to the diagnosis of the pregnancy related hypertensive disorder).

By "increase" is meant the ability to cause an overall elevation of 10%, 25%, 40%, 50%, 60%, 70%, 80%, 90%, or greater, in the level of polypeptide or nucleic acid, detected by the aforementioned assays (see "expression") or the biological activity of the polypeptide, detected by the aforementioned assays (see "biological activity"), as compared to a reference sample.

By "operably linked" is meant that a gene and a regulatory sequence(s) are connected in such a way as to permit gene expression when the appropriate molecules (e.g., transcriptional activator proteins) are bound to the regulatory sequence(s).

By "pharmaceutically acceptable carrier" is meant a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in Remington's Pharmaceutical Sciences, ($20^{th}$ edition), ed. A. Gennaro, 2000, Lippincott, Williams & Wilkins, Philadelphia, Pa.

By "an isolated protein" is meant a protein preparation that is substantially free (e.g,. 50%, 60%, 70%, 80%, 90% or more, by weight) from other proteins or compounds associated with the tissue from which the protein is obtained.

By "polymorphism" is meant a genetic variation, mutation, deletion or addition in a nucleic acid molecule encoding a polypeptide of the invention that is indicative of a predisposition to develop pre-eclampsia or eclampsia. A polymorphism may be present in the promoter sequence, an open reading frame, intronic sequence, or untranslated 3' region of a gene. Possible polymorphisms in the COMT gene include a missense G to A mutation that results in a substitution of methionine for valine at codons 108 and/or 158. See, for example, Wonodi et al., *Am. J Med. Genet.* 120B:47-50, 2003; Kirov et al., *Mol. Psychiatry* 3:342-345, 1998; Chen et al., *Am. J. Psychiatry* 156: 1273-1275, 1999; and Cotton et al., *J. Biol. Chem.* 279:23710-23718, 2004).

By "pre-eclampsia" is meant the multi-system disorder that is characterized by hypertension with proteinuria or edema, or both, glomerular dysfunction, brain edema, liver edema, or coagulation abnormalities due to pregnancy or the influence of a recent pregnancy. Pre-eclampsia generally occurs after the $20^{th}$ week of gestation. Pre-eclampsia is generally defined as some combination of the following symptoms: (1) a systolic blood pressure (BP) >140 mmHg and a diastolic BP >90 mmHg after 20 weeks gestation (generally measured on two occasions, 4-168 hours apart), (2) new onset proteinuria (1+ by dipstik on urinanaysis, >300 mg of protein in a 24-hour urine collection, or a single random urine sample having a protein/creatinine ratio >0.3), and (3) resolution of hypertension and proteinuria by 12 weeks postpartum. Severe pre-eclampsia is generally defined as (1) a diastolic BP >110 mmHg (generally measured on two occasions, 4-168 hours apart) or (2) proteinuria characterized by a measurement of 3.5 g or more protein in a 24-hour urine collection or two random urine specimens with at least 3+ protein by dipstick. In pre-eclampsia, hypertension and proteinuria generally occur within seven days of each other. In severe pre-eclampsia, severe hypertension, severe proteinuria and HELLP syndrome (hemolysis, elevated liver enzymes, low platelets) or eclampsia can occur simultaneously or only one symptom at a time. Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral edema and cerebral hemorrhage). The etiology of the seizures is thought to be secondary to the development of cerebral edema and focal spasm of small blood vessels in the kidney.

By "pregnancy related hypertensive disorder" is meant any condition or disease or pregnancy that is associated with or characterized by an increase in blood pressure. Included among these conditions are pre-eclampsia (including premature pre-eclampsia, severe pre-eclampsia), eclampsia, gestational hypertension, HELLP syndrome, (hemolysis, elevated liver enzymes, low platelets), abruption placenta, chronic hypertension, pregnancy with intra uterine growth restriction, and pregnancy with a small for gestational age (SGA) infant. It should be noted that although pregnancy with a SGA infant is not often associated with hypertension, it is included in this definition.

By "protein" or "polypeptide" or "polypeptide fragment" is meant any chain of more than two amino acids, regardless of post-translational modification (e.g., glycosylation or phosphorylation), constituting all or part of a naturally occurring polypeptide or peptide, or constituting a non-naturally occurring polypeptide or peptide.

By "reference sample" is meant any sample, standard, or level that is used for comparison purposes. A "normal reference sample" can be a prior sample taken from the same subject, a sample from a pregnant subject not having any pregnancy related hypertensive disorder, such as pre-eclampsia or eclampsia, a subject that is pregnant but the sample was taken early in pregnancy (e.g., in the first or second trimester or before the detection of a pregnancy related hypertensive disorder, such as pre-eclampsia or eclampsia), a subject that is pregnant and has no history of a pregnancy related hypertensive disorder, such as pre-eclampsia or eclampsia, a subject that is not pregnant, a sample of a purified reference polypeptide at a known normal concentration (i.e., not indicative of a pregnancy related hypertensive disorder, such as pre-eclampsia or eclampsia). By "reference standard or level" is meant a value or number derived from a reference sample. A normal reference standard or level can be a value or number derived from a normal subject. Desirably, all reference samples, standard, and levels are matched to the sample subject by at least one of the following criteria: gestational age of the fetus, maternal age, maternal blood pressure prior to pregnancy, maternal blood pressure during pregnancy, BMI of the mother, weight of the fetus. prior diagnosis of a pregnancy related hypertensive disorder, and a family history of a pregnancy related hypertensive disorder. A "positive reference" sample, standard or value is a sample or value or number derived from a subject that is known to have or to have had a pregnancy related hypertensive disorder, such as pre-eclampsia or eclampsia. The reference standard or level can also reflect the average or mean value of the level of the nucleic acid, polypeptide, or small molecule from normal reference subjects or positive reference subjects depending on the context. The reference can also be a chart, a graph, or a standard curve representing normal reference levels of the polypeptide, nucleic acid, or small molecule at any and/or all stages of pregnancy (e.g., weekly). Desirably, all reference samples, standard, and levels are matched to the sample subject by at least one of the following criteria: gestational age of the fetus, maternal age, maternal blood pressure prior to pregnancy, maternal blood pressure during pregnancy, BMI of the mother, weight of the fetus, prior diagnosis of a pregnancy related hypertensive disorder, and a family history of a pregnancy related hypertensive disorder.

By "reduce or inhibit" is meant the ability to cause an overall decrease preferably of 10% or greater, more preferably of 20%, 40%, 50%, 60%, 70%, 80%, 90% or greater change in the level of protein or nucleic acid, detected by the aforementioned assays (see "expression"), as compared to an untreated sample By "sample" is meant a tissue biopsy (e.g., placental tissue), chorionic villus sample, cell, bodily fluid (e.g., blood, serum, plasma, urine, saliva, amniotic fluid, or cerebrospinal fluid) or other specimen obtained from a subject. Desirably, the biological sample includes COMT nucleic acid molecules or polypeptides or both.

By "specifically binds" is meant a compound or antibody which recognizes and binds a polypeptide of the invention but that does not substantially recognize and bind other molecules in a sample, for example, a biological sample, which naturally includes a polypeptide of the invention.

By "subject" is meant a mammal, including, but not limited to, a human or non-human mammal, such as a cow, a horse, a sheep, a pig, a goat, a dog, or a cat. Included in this definition are pregnant, post-partum, and non-pregnant mammals.

By "symptoms of pre-eclampsia" is meant any of the following: (1) a systolic blood pressure (BP) >140 mmHg and a diastolic BP >90 mmHg after 20 weeks gestation, (2) new onset proteinuria (1+ by dipstik on urinalysis, >300 mg of protein in a 24 hour urine collection, or random urine protein/creatinine ratio >0.3), and (3) resolution of hypertension and proteinuria by 12 weeks postpartum. The symptoms of pre-eclampsia can also include renal dysfunction and glomerular endotheliosis or hypertrophy. By "symptoms of eclampsia" is meant the development of any of the following symptoms due to pregnancy or the influence of a recent pregnancy: seizures, coma, thrombocytopenia, liver edema, pulmonary edema, and cerebral edema.

By "therapeutic amount" is meant an amount that when administered to a patient suffering from pre-eclampsia or eclampsia is sufficient to cause a qualitative or quantitative reduction in the symptoms of pre-eclampsia or eclampsia as described herein.

By "treating" is meant administering a compound or a pharmaceutical composition for prophylactic and/or therapeutic purposes. To "treat disease" or use for "therapeutic treatment" refers to administering treatment to a subject already suffering from a disease to improve the subject's condition. Preferably, the subject is diagnosed as suffering from pre-eclampsia or eclampsia based on identification of any of the characteristic symptoms described below or the use of the diagnostic methods described herein. To "prevent disease" refers to prophylactic treatment of a subject who is not yet ill, but who is susceptible to, or otherwise at risk of, developing a particular disease. Preferably a subject is determined to be at risk of developing a pregnancy related disorder, such as gestational hypertension, pre-eclampsia, or eclampsia using the diagnostic methods described herein. Thus, in the claims and embodiments, treating is the administration to a mammal either for therapeutic or prophylactic purposes.

Other features and advantages of the invention will be apparent from the following description of the preferred embodiments thereof, and from the claims.

BRIEF DESCRIPTION OF THE DRAWINGS

FIG. 12 is a table showing that the administration of 2-ME does not alter the litter size or cause abnormal development.

DETAILED DESCRIPTION OF THE INVENTION

Figure 1:
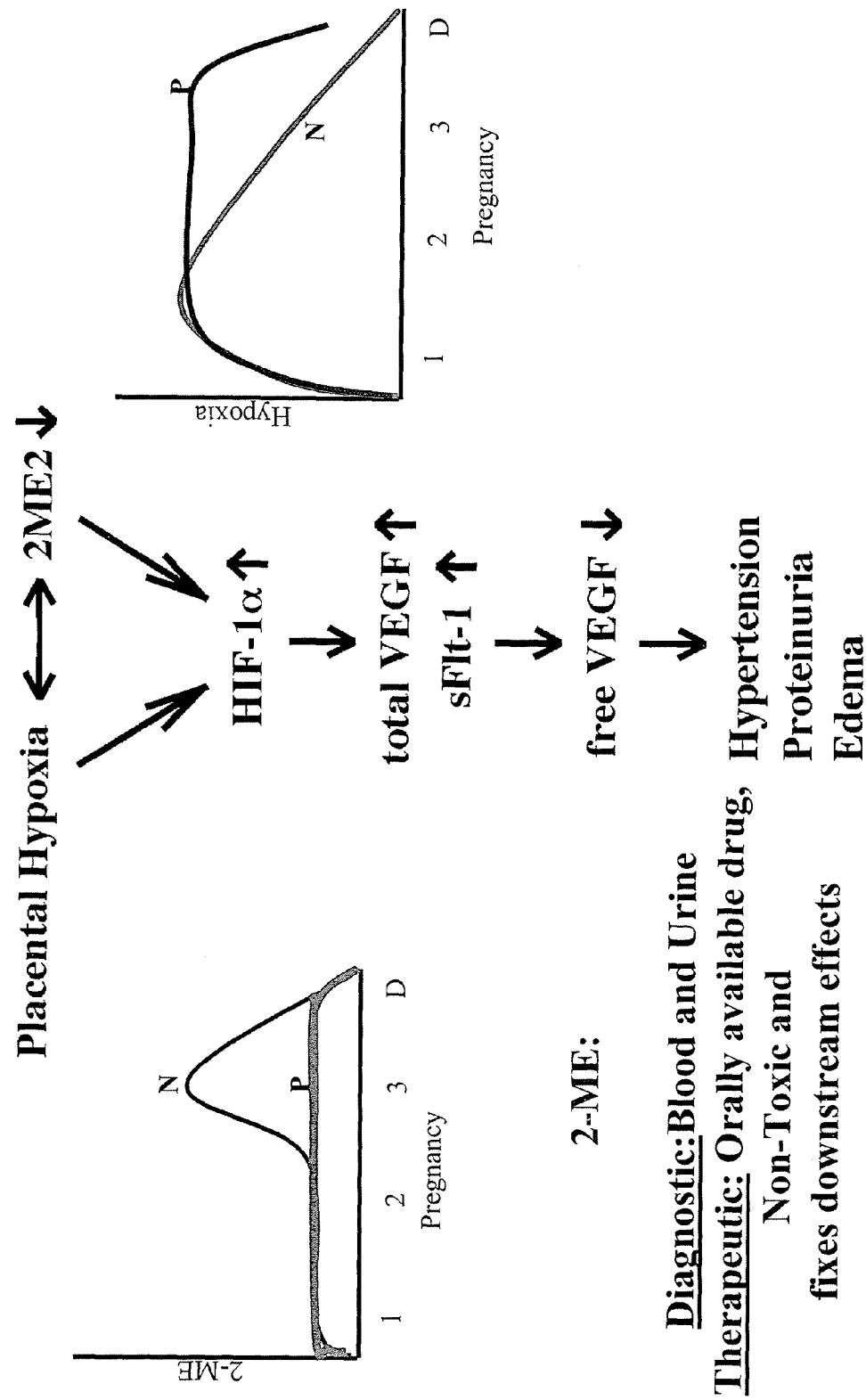
FIG. 1 is a schematic of the hypoxia pathway involved in placental hypoxia.

Placental hypoxia is a key determinant associated with the pathogenesis of pregnancy related hypertensive disorders, such as pre-eclampsia and eclampsia (FIG. 1). We have discovered that measurement of the expression of certain genes involved in the hypoxic pathway is useful for the diagnosis of pre-eclampsia or eclampsia. Furthermore, compounds which modulate the activity of these genes may be useful as therapeutic compounds to treat pregnancy related hypertensive disorders, such as pre-eclampsia and eclampsia.

I. Hypoxia Related Genes

A hypoxic condition relating to pregnancy related hypertensive disorders such as pre-eclampsia or eclampsia can be a result of any of the following, either alone or in combination: a change in the number of copies of one or more genes required for blood or oxygen transport to the placenta or the fetus; a change in the level of expression of one or more genes required for blood or oxygen transport to the placenta or the fetus; a change in metabolic processes and the levels of their substrates, products, or by-products (i.e., metabolic indicators of a hypoxic condition).

Catechol-O-methyltransferase

Figure 2:
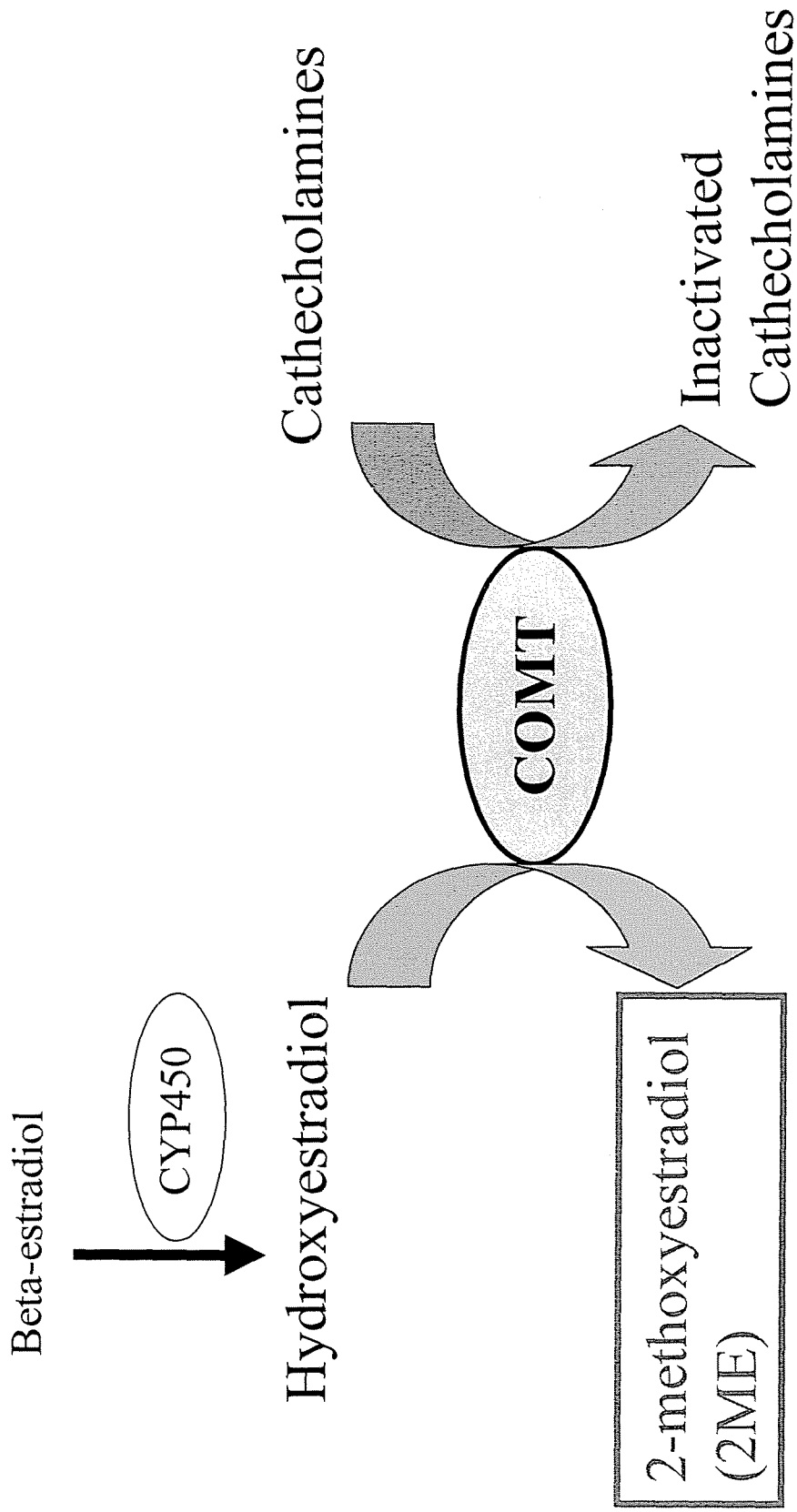
FIG. 2 is a schematic of the activity of the Catechol-O-methyltransferase (COMT) enzyme.
Figure 3:
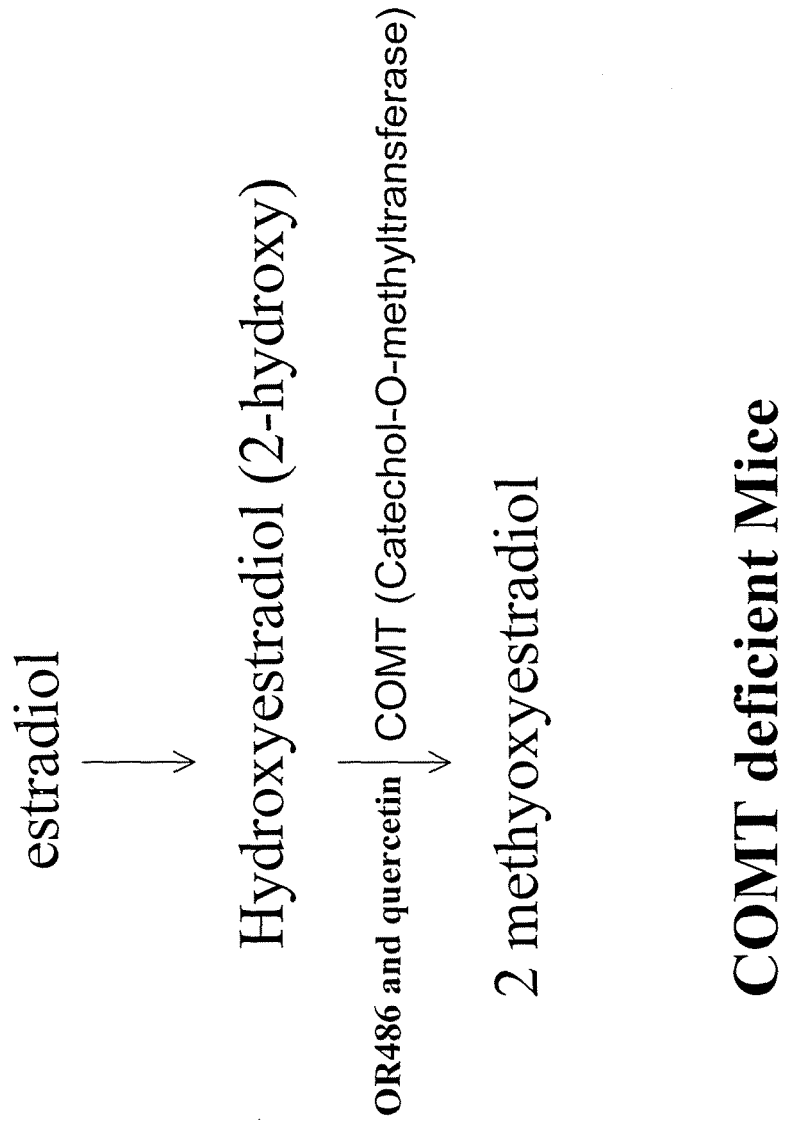
FIG. 3 is a schematic of the role of COMT in placental hypoxia.

In the present invention, we have discovered that catechol-O-methyltransferase (COMT), which catalyzes the conversion of 2 hydroxyestradiol to 2-ME, is decreased in women with pre-eclampsia or eclampsia (FIGS. 2 and 3). While previously a role for COMT in hypoxia had not been established, COMT had been implicated in schizophrenia. It is believed that in neural tissue COMT is one of the enzymes that degrade catecholamine neurotransmitters. Certain polymorphisms of COMT have been associated with an elevated risk of developing schizophrenia and several inhibitors of COMT have been developed in order to treat schizophrenia.

Other Hypoxia Related Factors

Hypoxia-Inducible Factor 1 (HIF-1) is a transcription factor that has been shown to play an essential role in cellular responses to hypoxia. Upon hypoxic stimulation, HIF-1 has been shown to activate genes that contain Hypoxic Response Elements (HREs) in their promoters, and thus up-regulate a series of gene products that promote cell survival under conditions of low oxygen availability. The list of known HIF-responsive genes includes glycolytic enzymes (such as lactate dehydrogenase (LDH-A), enolase-1 (ENO-I), and aldolase A), glucose transporters (GLUT 1 & 3), vascular endothelial growth factor (VEGF), inducible nitric oxide synthase (NOS-2), and erythropoietin (EPO). The switch of the cell to anaerobic glycolysis, and the up-regulation of angiogenesis by VEGF is geared at maximizing cell survival under conditions of low oxygen tension by reducing the requirement for oxygen, and increasing vasculature to maximize oxygen delivery to tissues. The HIF-1 transcription complex has recently been shown to comprise a heterodimer of two basic helix-loop-helix proteins, HIF-1 α and HIF-1 β (also known as ARNT, Aryl Hydrocarbon Receptor Nuclear Translocator). HIF-1α is a member of the basic-helix-loop-helix PAS domain protein family and is an approximately 120 kDa protein containing two transactivation domains (TAD) in its carboxy-terminal half and DNA binding activity located in the N-terminal half of the molecule. HIF-1α is constitutively degraded by the ubiquitin-proteosome pathway under conditions of normoxia, a process that is facilitated by binding of the von Hippel-Lindau (VHL) tumor suppressor protein to HIF-1α. Under conditions of hypoxia, degradation of HIF-1α is blocked and active HIF-1 α accumulates. The subsequent dimerization of HIF-1 α a with ARNT leads to the formation of active HIF transcription complexes in the nucleus, which can bind to and activate HREs on HIF-responsive genes.

2-Methoxyestradiol (2-ME) is an endogenous metabolite of estradiol (E2) that has potent anti-proliferative activity and induces apoptosis in a wide variety of tumor and non-tumor cell lines. When administered orally, it exhibits antitumor and antiangiogenic activity with little or no toxicity. Currently, 2-ME is in several phase-I and II clinical trials for cancer therapies under the name PANZEM™. 2-ME has been shown to downregulate HIF-1 at the posttranscriptional level and inhibits HIF-1 induced transcriptional activation of VEGF expression.

We have previously discovered that 2-methoxyestradiol (2-ME), a natural metabolite of estradiol, may be used as a therapeutic agent for pre-eclampsia and other pregnancy related disorders which are associated with high expression of sFlt1 which reduces the levels of free VEGF. Blocking of circulating VEGF leads to proteinuria (Sugimoto et al., J. Biol. Chem. (2003) 278:12605-8). 2-methoxyestradiol is significantly decreased (up to 6-7 fold) in the circulation of pregnant women with pre-eclampsia in the second and third trimesters of pregnancy as compared to non-preeclamptic women. 2-methoxyestradiol decreases the expression of HIF-1α in cytotrophoblasts from the placenta which leads to a dramatic decrease in the expression of VEGF, PlGF, VEGF Receptor 1 (VEGFR1) and sFlt-1 (see FIG. 1 and PCT Application Publication No. WO 2005/110462 A2, which is hereby incorporated by reference in its entirety).

II. Diagnostics

Diagnostic methods of the invention comprise assaying one or more biological samples obtained from an individual for polymorphisms in a gene involved in pre-eclampsia (e.g., COMT) or for difference in the levels of a substance (e.g., genes, gene products, metabolites (e.g., a substrate of a metabolic reaction), or metabolic by-products) that is known to be involved in the hypoxia pathway (e.g., COMT) in the placenta and determining whether they are greater or less than a reference sample taken either from the same patient at a previous time or from a subject known to not have or be at risk for pre-eclampsia or eclampsia.

The present invention features assays based on the detection of any one or more of the proteins, nucleic acids, or small molecules that are involved in the induction of hypoxia, including those described above (e.g., COMT), to diagnose pre-eclampsia, eclampsia, or the propensity to develop such conditions. Preferably the invention includes the detection of COMT protein or nucleic acid. The present invention also features diagnostic assays based on the detection of at least one, at least two, at least three, at least four, or at least five or more of the proteins or small molecules that are involved in the induction of hypoxia to diagnose pre-eclampsia, eclampsia, or the propensity to develop such conditions.

Methods of diagnosis can involve genomic analysis to determine whether there are mutations in hypoxia-associated genes (e.g., COMT), analysis of mRNA and protein expression levels to see if there are aberrant levels of hypoxia-associated proteins, and activity assays to determine whether there is abnormal activity of hypoxia associated proteins.

In one embodiment of the invention the diagnostic methods of the invention include determining the nucleic acid sequence of a gene encoding a protein involved in the induction of hypoxia (e.g., COMT), wherein an alteration in the subject's nucleic acid sequence that is an alteration that changes (i.e., increase or decreases) the expression level or biological activity of the gene product in the subject diagnoses the subject with pre-eclampsia or eclampsia, or a propensity to develop pre-eclampsia or eclampsia. Such genetic alterations may be present in the promoter sequence, an open reading frame, intronic sequence, or untranslated 3' region of a gene. Information related to genetic alterations can be used to diagnose a subject as having pre-eclampsia, eclampsia, or a propensity to develop such conditions. As noted throughout, specific alterations in the levels of biological activity of any polypeptide of the invention or any combination thereof, can be correlated with the likelihood of pre-eclampsia or eclampsia, or the predisposition to the same. As a result, one skilled in the art, having detected a given mutation, can then assay one or more of the biological activities of the polypeptide to determine if the mutation causes or increases the likelihood of pre-eclampsia or eclampsia.

Examples of mutations in COMT known to reduce its enzymatic activity include a missense mutation that results in a valine to methionine substitution at amino acid 108 or 158 (Kirov et al., *Mol. Psychiatry* 3:342-345, 1998 and Chen et al., *Am. J. Psychiatry* 156:1273-1275, 1999).

Hypoxia associated proteins levels in biological samples can be assayed using any suitable method known in the art. For example, when a protein is an enzyme (e.g., COMT), the protein can be quantified based upon its catalytic activity or based upon the number of molecules of the protein contained in a sample. Standard methods may be used to measure levels of any one or more of the hypoxia associated proteins in any bodily fluid, including, but not limited to, urine, blood, serum, plasma, saliva, amniotic fluid, or cerebrospinal fluid. Such methods include immunoassay, ELISA, western blotting using antibodies directed to hypoxia associated proteins (e.g., COMT), radioimmunoassay (RIA) and quantitative enzyme immunoassay. Exemplary methods such as methods based upon activity, expression levels or metabolic indicators are described in U.S. Pat. No. 6,276,169. Methods of detecting nucleic acids, proteins and small molecules can also be found in Maniatis, T., et al., Molecular Cloning: Laboratory Manual, Cold Spring Harbor Laboratory, Cold Spring Harbor, N.Y. (1982), and Sambrook, J. et al., Molecular Cloning: A Laboratory Manual, Cold Spring Harbor Laboratory, Cold Spring Harbor, N.Y. (1989).

For example, a protein-specific monoclonal antibody, can be used both as an immunoadsorbent and as an enzyme-labeled probe to detect and quantify a protein of interest. The amount of such protein present in a sample can be calculated by reference to the amount present in a standard preparation using a linear regression computer algorithm (see Iacobilli et al., Breast Cancer Research and Treatment, 11:19-30 (1988)). In another embodiment, two different monoclonal antibodies to the protein of interest can be employed, one as the immunoadsorbent and the other as an enzyme-labeled probe.

Exemplary methods used to measure the mRNA level of a hypoxia associated protein include northern blot analysis, SI nuclease mapping, polymerase chain reaction (PCR), quantitative reverse transcription in combination with the polymerase chain reaction (RT-PCR), reverse transcription in combination with ligase chain reaction (RT-LCR) and PCR or LCR in combination with hybridization.

In addition, indirect methods for assessing whether a tissue sample has been subjected to hypoxia can also be employed, such as assessing cells for altered cell adhesion and cellular invasion assays, as described in U.S. Pat. No. 6,276,169. In one example, the method for detecting hypoxia in an individual as a diagnostic indictor of pre-eclampsia or eclampsia, includes isolating cells from the individual and evaluating the invasiveness of the cell in an in vitro assay as described therein. In this embodiment, an increase (e.g., by 10%, 20%, 30%, 40%, 50%, 60%, 70%, 80%, 90% or more) in invasiveness indicates that the cells have undergone hypoxia and is considered a diagnostic indicator of pre-eclampsia or eclampsia.

Diagnostic methods also include measuring the enzymatic activity of COMT (e.g., the method set forth in Chen et al., supra, and described above). Decreases in COMT activity (e.g., by 10%, 20%, 30%, 40%, 50%, 60%, 70%, 80%, 90% or more) is indicative of a pregnancy related hypertensive disorder.

Samples to be measured include any tissue, preferably from the placenta, cells, or any bodily fluid, including, but not limited to, urine, blood, serum, plasma, saliva, amniotic fluid, or cerebrospinal fluid. It is appreciated that some substances which are suitable indicators of hypoxia are not found in all biological samples. Thus, the substance or substances to be measured will be selected based upon the nature of the biological sample.

In another embodiment, hybridization with PCR probes that are capable of detecting a nucleic acid molecule encoding a hypoxia associated proteins, including genomic sequences, or closely related molecules, may be used to hybridize to a nucleic acid sequence derived from a subject having pre-eclampsia or eclampsia or at risk of developing such conditions. The specificity of the probe, whether it is made from a highly specific region, e.g., the 5' regulatory region, or from a less specific region, e.g., a conserved motif, and the stringency of the hybridization or amplification (maximal, high, intermediate, or low), determine whether the probe hybridizes to a naturally occurring sequence, allelic variants, or other related sequences. Hybridization techniques may be used to identify mutations indicative of a pre-eclampsia or eclampsia or may be used to monitor expression levels of a gene encoding a soluble endoglin polypeptide (for example, by Northern analysis, Ausubel et al., supra).

In one embodiment, a subject sample of a bodily fluid (e.g., urine, plasma, serum, amniotic fluid, or cerebrospinal fluid) is collected early in pregnancy prior to the onset of pre-eclampsia symptoms. In another example, the sample can be a tissue or cell collected early in pregnancy prior to the onset of pre-eclampsia symptoms. Non-limiting examples include placental tissue, placental cells, endothelial cells, and leukocytes such as monocytes. In humans, for example, maternal blood serum samples are collected from the antecubital vein of pregnant women during the first, second, or third trimesters of the pregnancy. Preferably, the assay is carried out during the first trimester, for example, at 4, 6, 8, 10, or 12 weeks, or during the second trimester, for example at 14, 16, 18, 20, 22, or 24 weeks. Such assays may also be conducted at the end of the second trimester or the third trimester, for example at 26, 28, 30, 32, 34, 36, or 38 weeks. It is preferable that levels of one or more hypoxia associated proteins be measured twice during this period of time. For the diagnosis of post-partum pre-eclampsia or eclampsia, the assay is carried out postpartum. For the diagnosis of a propensity to develop pre-eclampsia or eclampsia, the assay is carried out prior to the onset of pregnancy. In one example, for the monitoring and management of therapy, the assay is carried out after the diagnosis of pre-eclampsia but during the pregnancy.

In one particular example, serial blood samples can be collected during pregnancy and the levels of at least one hypoxia associated protein determined by ELISA. An increase or decrease (e.g., by at least 10%, 20%, 30%, 40%, 50%, 60%, 70%, 80%, 90% or more), over time is indicative of pre-eclampsia or eclampsia, or the propensity to develop either.

In another example, a sample is collected during the second trimester and early in the third trimester and in increase or decrease in the level of a hypoxia associated protein from the first sampling to the next is indicative of pre-eclampsia or eclampsia, or the propensity to develop either. Preferably the method includes the detection of COMT.

In veterinary practice, assays may be carried out at any time during the pregnancy, but are, preferably, carried out early in pregnancy, prior to the onset of pre-eclampsia symptoms. Given that the term of pregnancies varies widely between species, the timing of the assay will be determined by a veterinarian, but will generally correspond to the timing of assays during a human pregnancy.

The diagnostic methods described herein can be used individually or in combination with any other diagnostic method described herein for a more accurate diagnosis of the presence of, severity of, or estimated time of onset of pre-eclampsia or eclampsia. In addition, the diagnostic methods described herein can be used in combination with any other diagnostic methods determined to be useful for the accurate diagnosis of the presence of, severity of, or estimated time of onset of pre-eclampsia or eclampsia. The diagnostic methods described herein can also be used to monitor and manage pre-eclampsia or eclampsia in a subject.

In one example, the assays and methods described above are used to diagnose pre-eclampsia or eclampsia in a patient having or having a propensity to develop schizophrenia or to predict the likelihood of developing pre-eclampsia or eclampsia should the patient become pregnant. Mutations in the COMT gene are known to be associated with schizophrenia (see for example, Wonodi et al., Am. J. Med. Genet. 120B: 47-50, 2003; Kirov et al., Mol. Psychiatry 3:342-345, 1998; and Chen et al., Am. J. Psychiatry 156: 1273-1275, 1999), but there are conflicting reports as to the increased risk of pre-eclampsia in women having or having a propensity to develop schizophrenia (Kendell et al., Br. J. Psychiatry 168:556-561, 1996 and Bennedsen et al., Schizophr. Res. 47:167-175, 2001). The invention described herein demonstrates that COMT levels or biological activity is decreased in subjects having, or at risk for developing, pre-eclampsia or eclampsia. Therefore, using the methods described herein, samples from subjects having schizophrenia can be assayed to determine if a polymorphism or a mutation in the COMT gene is present, and if present, if such a mutation leads to a decrease in the levels or activity of COMT. The detection of such a polymorphism or mutation could assist the clinician in advising the subject prior to becoming pregnant and could also assist the clinician in monitoring the pregnancy to prevent the development of pre-eclampsia or to diagnose the pre-eclampsia at an early stage.

For any of the diagnostic assays described, the level of nucleic acid or polypeptide or the biological activity of COMT can be measured prior to pregnancy to establish a baseline value or to predict the likelihood of development of pre-eclampsia (e.g., if a polymorphism is detected), during the first trimester, for example, at 4, 6, 8, 10, or 12 weeks, or during the second trimester, for example at 14, 16, 18, 20, 22, or 24 weeks. Such assays may also be conducted at the end of the second trimester or the third trimester, for example at 26, 28, 30, 32, 34, 36, or 38 weeks. Such assays can also be conducted on a regular basis (e.g., every week, every two weeks, every three weeks, every four weeks or less often) to monitor a women having or having a propensity to develop pre-eclampsia or eclampsia throughout the pregnancy. In one embodiment, the assay is conducted at least once early in the pregnancy (e.g., first trimester or first half of the second trimester) and at least once later in pregnancy (e.g., towards the second half of the second trimester or the third trimester).

Diagnostic Kits

The invention also provides for a diagnostic test kit. For example, a diagnostic test kit can include antibodies to any hypoxia associated protein (e.g., COMT) and components for detecting, and more preferably evaluating, binding between the antibodies and hypoxia associated protein. For detection, either the antibody or the hypoxia associated protein is labeled, and either the antibody or the polypeptide of the invention is substrate-bound, such that polypeptide of the invention-antibody interaction can be established by determining the amount of label attached to the substrate following binding between the antibody and the polypeptide of the invention. A conventional ELISA is a common, art-known method for detecting antibody-substrate interaction and can be provided with the kit of the invention. Hypoxia associated proteins can be detected in virtually any bodily fluid including, but not limited to urine, serum, plasma, saliva, amniotic fluid, or cerebrospinal fluid. The invention also provides for a diagnostic test kit that includes a nucleic acid encoding a hypoxia associated protein that can be used to detect and determine levels of nucleic acids encoding a hypoxia associated protein. A kit that determines an alteration in the level of a hypoxia associated protein relative to a reference, such as the level present in a normal control, is useful as a diagnostic kit in the methods of the invention.

III. Gene Therapy

Also included in the invention is the treatment of patients diagnosed with (e.g., using the diagnostic methods described above) or at risk for developing pre-eclampsia with gene therapy. In these cases, gene therapy is used to increase expression of hypoxia associated genes (i.e., genes that have aberrant decreases in activity, leading to hypoxia) or used to decrease the expression of hypoxia genes (i.e., genes that have aberrant increases in activity, leading to hypoxia).

In the case where an increase of activity of a particular gene is desired (e.g., COMT), gene therapy approaches can be used to introduce hypoxia-associated genes into cells in vivo. In the case where a decrease of activity of a particular gene is desired, constructs designed to inhibit the expression of a desired gene can be used (e.g., antisense, siRNA or RNAi constructs).

Numerous methods for gene therapy are well known in the art and can be used in the invention. These approaches can employ vectors such as viral vectors (DNA or RNA) and plasmid vectors, and/or chemical means. Examples of different approaches that can be used in the gene therapy methods of the invention are described as follows.

One example of a viral vector-based gene therapy approach that can be used in the invention employs adeno-associated virus (AAV) vectors, which can achieve latent infection of a broad range of cell types, resulting in persistent expression of a therapeutic gene such as a COMT gene in a subject. As examples, the following AAV vectors can be used: AAV1, AAV2, AAV3, AAV4, AAV5, and AAV6 (Lee et al., Biochem. J. 387:1, 2005). The capsid protein of these vectors can, optionally, be genetically modified, if desired, to direct infection towards a particular tissue type (Lieber, Nature Biotechnology 21:1011, 2003).

Other examples of virus vector-based approaches employ adenoviruses, which infect a wide variety of cell types, including non-dividing cells. The invention includes the use of any one of more than 50 serotypes of adenoviruses that are known in the art, including the most commonly used serotypes for gene therapy: type 2 and type 5. To increase the efficacy of gene expression and prevent unintended spread of the virus, adenoviruses can include genetic modifications, such as E1 region deletions, E1 region and E2 and/or E4 region deletions, or deletion of the entire adenovirus genome except for the cis-acting inverted terminal repeats and a packaging signal (Gardlik et al., Med. Sci. Monit. 11:RA110, 2005). Any adenoviral vectors including such modifications can be used in the invention.

The invention also includes the use of retroviral vectors including, for example, Moloney Murine Leukemia Virus (MoMLV). These vectors can include genetic modifications including, e.g., deletions of the gag, pol, and/or env genes, as is known in the art. Using retrovirus constructs, gene therapy vectors can be targeted to specific tissues or cells. This can be achieved by the fusion of part of the retrovirus env gene to a sequence encoding the ligand for a tissue-specific receptor. A specific type of retrovirus vector that can be used in the invention is lentivirus vectors, which can infect both proliferating and quiescent cells. An exemplary lentivirus vector for use in gene therapy is HIV-1. Previously constructed genetic modifications of lentiviruses, which can be used in vectors of the present invention, include deletions of all protein encoding genes except those encoding gag, pol, and rev (Moreau-Gaudry et al., Blood 98:2664, 2001).

In addition to the viral vectors described above, other viral vectors that can be used in the invention include, for example, vaccinia virus, bovine papilloma virus, and herpes virus, such as Epstein-Barr Virus vectors. (Also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107: 77S-83S, 1995.)

Gene therapy methods employing chemical means for introducing nucleic acid molecules into cells can also be used in the methods of the invention. In one example, cationic liposomes are used. Exemplary cationic liposomes for use in the invention include DOTMA, DOPE, DOSPA, DOTAP, DC-Chol, Lipid GL67™, and EDMPC. These chemicals can be used individually or in combination to transfect cells with a vector, such as a plasmid, that has been constructed to express a gene of interest such as COMT. Other approaches that can be used in the invention involve the use of lipofection (Felgner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983) or asialoorosomucoid-polylysine conjugation (Wu et al., J. Biol. Chem. 263:14621, 1988; Wu et al., J. Biol. Chem. 264:16985, 1989).

In other methods, DNA-polymer conjugates can be used to express a protein of interest, such as COMT, in a patient. In such approaches, a vector constructed to express COMT is combined with a polymer to achieve expression of COMT without the use of a viral vector. Exemplary compounds for use in this approach are polyethyleneimine (PEI), polylysine, polylysine linked to nuclear localization signals, polyamidoamine, and polyarginine ($Arg_{16}$). Another method of gene therapy that can be used in the invention employs a substantially purified DNA vector (naked DNA) for the expression of COMT in a subject. Such a DNA vector can be administered by injection, use of a gene gun, or electroporation.

In the chemical-based, non-viral approaches described above, the therapeutic material can be directed to certain tissue types. For example, the material can include antibodies, such as multivalent antibodies, receptor ligands, or carbohydrates that direct the materials to the desired tissue.

In the case of ex vivo gene therapy, the vectors described above can be administered directly to cells in culture (e.g., hematopoietic cells and placental cells), which can be obtained from the patient or from a donor. In addition to such vector-based methods, gene transfer into such cells can be achieved non-vector-based methods such as those described above, as well as transfection methods involving the use of calcium phosphate, DEAF dextran, electroporation, or protoplast fusion.

In general, ex vivo gene therapy results in expression of a therapeutic gene, such as COMT, only in a particular, desired tissue. In such applications, the vectors described above can be constructed so as to constitutively express COMT. Numerous constitutive regulatory elements that can be used in such constructs are well known in the art. For example, certain elements present in the native viruses described above can be used to constitutively express a gene of interest. Other examples of constitutive regulatory elements that can be used in the invention include β-actin, EF1, EGR1, eIF4A1, FerH, FerL, GAPDH, GRP78, GRP94, HSP70, beta-Kin, ROSA, and ubiquitin B promoters. For in vivo applications, the vectors described above can, if desired, be modified to include regulatory elements that confine the expression of COMT to certain tissue types, such as placental cells. Numerous examples of regulatory elements specific to certain tissue types are well known in the art.

In addition to constitutive and cell/tissue-specific promoters, the gene therapy methods of the invention can employ inducible promoters. In one example of such an approach, cells are transfected with multiple viral or plasmid vectors. Typically a first vector expresses a gene of interest, such as COMT, under the control of a regulatory element that is responsive to the expression product of a second vector. The activity of this expression product is controlled by the addition or administration of a pharmacological compound or other exogenous stimulation. Examples of these systems are those including the following inducing agents or conditions: tetracycline, mifepristone, ponasterone A, papamycin, tamoxifen, radiation, and heat shock (Robson et al., J. Biomed. Biotechnol. 2:110, 2003).

IV. Protein Therapy

In one embodiment of the present invention, purified forms of COMT is administered to the subject in order to treat or prevent a pregnancy related hypertensive disorder such as pre-eclampsia or eclampsia.

Purified COMT includes any protein with an amino acid sequence that is homologous, more desirably, substantially identical to the amino acid sequence of COMT, that has at least 80% of the biological activity of COMT as measured using the assay set forth in Chen et al., supra, and set forth above.

V. Screening Assays

One aspect of the invention features a screen for compounds that reduce placenta hypoxia. Such compounds would be useful, for example, for treating pre-eclampsia.

One method of the invention is a screen for an activator for COMT. Examples of activators of COMT are compounds that increase the expression and/or biological activity of COMT.

The methods of the invention also include screens for modulators of the expression and/or biological activity of other hypoxia associated proteins. These proteins include HIF-1α, 2-ME, VEGF (free or total), sFlt-1, PlGF, EPO, LDH-A, ET-1, transferrin, transferrin receptor, and Flk-1.

Screening assays to identify compounds that modulate the expression or activity of hypoxia-associated proteins are carried out by standard methods. The screening methods may involve high-throughput techniques. In addition, these screening techniques may be carried out in cultured cells or in organisms such as worms, flies, yeast, or mammals. Screening in these organisms may include the use of polynucleotides homologous to hypoxia-associated proteins.

Any number of methods is available for carrying out such screening assays. According to one approach, candidate compounds are added at varying concentrations to the culture medium of cells expressing a polynucleotide coding hypoxia-associated proteins. There are several art-known methods to assay for gene expression. Some examples include the preparation of RNA from samples and the use of the RNA for northern blotting, PCR based amplification, or RNAse protection assays. The level of gene expression in the presence of the candidate compound is compared to the level measured in a control culture medium lacking the candidate molecule. A compound which promotes a change in hypoxia-associated proteins is considered useful in the invention; such a molecule may be used, for example, as a therapeutic for pre-eclampsia.

While a candidate compound may be identified through modulation of any hypoxia-associated protein, particularly promising compounds would modulate several, or many hypoxia-associated proteins. It is well known in the art that the gene expression of a large number of genes can be measured using a nucleotide microarray. Compounds which modulate hypoxia-associated proteins could be identified by comparing the expression profile of hypoxia-associated genes from cells treated with a candidate compound compared to a control sample.

If desired, the effect of candidate compounds may, in the alternative, be measured at the level of polypeptide production using the same general approach and standard immunological techniques, such as Western blotting or immunoprecipitation with an antibody specific for a hypoxia-associated protein. For example, immunoassays may be used to detect or monitor the expression of hypoxia-associated proteins. Polyclonal or monoclonal antibodies that are capable of binding to such a polypeptide may be used in any standard immunoassay format (e.g., ELISA, Western blot, RIA assay, or protein microarray) to measure the level of hypoxia-associated proteins. A compound that promotes a change in the expression of hypoxia-associated proteins is considered particularly useful. Again, such a molecule may be used, for example, as a therapeutic for pre-eclampsia.

Alternatively, or in addition, candidate compounds may be screened for those that specifically bind to and modulate the activity of hypoxia-associated proteins (e.g., a compound which specifically binds and activates COMT). The efficacy of such a candidate compound is dependent upon its ability to interact with the polypeptide. Such an interaction can be readily assayed using any number of standard binding techniques and functional assays (e.g., those described in Ausubel et al., supra). For example, a candidate compound may be tested in vitro for interaction and binding with hypoxia-associated proteins and its ability to modulate its activity may be assayed by any standard assays (e.g., those described herein).

In one particular embodiment, a candidate compound that binds to hypoxia-associated proteins may be identified using a chromatography-based technique. For example, recombinant hypoxia-associated proteins may be purified by standard techniques from cells engineered to express hypoxia-associated proteins and may be immobilized on a column. A solution of candidate compounds is then passed through the column, and a compound specific for hypoxia-associated proteins is identified on the basis of its ability to bind to the polypeptide and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography). Compounds isolated by this approach may also be used, for example, as therapeutics to treat pre-eclampsia. Compounds that are identified as binding to hypoxia-associated proteins with an affinity constant less than or equal to 10 mM are considered particularly useful in the invention.

In one aspect, the invention features the use of mouse models of hypoxia, as described herein, to identify compounds useful for the treatment of pre-eclampsia. In order to evaluate the efficacy of a candidate compound in vivo, mice treated with a candidate compound are examined for indications of pre-eclampsia, for example, as described in the experimental results herein. These models can be used as an initial screen, or used to validate candidate compounds identified in other screens of the invention as described herein.

Potential agonists and antagonists include organic molecules, peptides, peptide mimetics, polypeptides, and antibodies that bind to hypoxia-associated proteins, or a polynucleotide encoding hypoxia-associated proteins, and thereby increase or decrease its activity. Potential agonists or antagonists include small molecules that bind to and occupy the binding sites hypoxia-associated proteins that are known to be enzymes. Other potential antagonists include antisense molecules.

Polynucleotide sequences coding for hypoxia-associated proteins may also be used in the discovery and development of compounds to treat pre-eclampsia. Hypoxia-associated proteins, upon expression, can be used as a target for the screening of drugs. Additionally, the polynucleotide sequences encoding the amino terminal regions of the encoded polypeptide or Shine-Delgarno or other translation facilitating sequences of the respective mRNA can be used to construct antisense sequences to control the expression of the coding sequence of interest. Polynucleotides encoding fragments of hypoxia-associated proteins may, for example, be expressed such that RNA interference takes place, thereby reducing expression or activity of hypoxia-associated proteins.

The antagonists and agonists of the invention may be employed, for instance, to treat pre-eclampsia.

Small molecules provide useful candidate therapeutics. Preferably, such molecules have a molecular weight below 2,000 daltons, more preferably between 300 and 1,000 daltons, and most preferably between 400 and 700 daltons. It is preferred that these small molecules are organic molecules.

Test Compounds and Extracts

In general, compounds capable of treating pre-eclampsia are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and polynucleotide-based compounds. Synthetic compound libraries are commercially available. Alternatively, libraries of natural compounds in the form of bacterial, fungal, plant, and animal extracts are commercially available. In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity in treating pre-eclampsia should be employed whenever possible.

When a crude extract is found to have an activity that modulates hypoxia-associated protein expression or activity, or a binding activity, further fractionation of the positive lead extract is necessary to isolate chemical constituents responsible for the observed effect. Thus, the goal of the extraction, fractionation, and purification process is the characterization and identification of a chemical entity within the crude extract having activity that may be useful in treating pre-eclampsia. Methods of fractionation and purification of such heterogenous extracts are known in the art. If desired, compounds shown to be useful agents for the treatment of pre-eclampsia are chemically modified according to methods known in the art.

VI. Methods of Treatment

Compounds identified as modulating hypoxia related proteins can be used to treat pre-eclampsia. Preferably, the therapeutic is administered during pregnancy for the treatment or prevention of pre-eclampsia or eclampsia or after pregnancy to treat post-partum pre-eclampsia or eclampsia.

Dosages and Modes of Administration

Techniques and dosages for administration vary depending on the type of compound (e.g., chemical compound, antibody, antisense, or nucleic acid vector) and are well known to those skilled in the art or are readily determined.

Therapeutic compounds of the present invention may be administered with a pharmaceutically acceptable diluent, carrier, or excipient, in unit dosage form. Administration may be parenteral, intravenous, subcutaneous, oral or local by direct injection into the amniotic fluid. Intravenous delivery by continuous infusion is the preferred method for administering the therapeutic compounds of the present invention. Therapeutic compounds of the invention can also be administered ex vivo.

The composition can be in the form of a pill, tablet, capsule, liquid, or sustained release tablet for oral administration; or a liquid for intravenous, subcutaneous or parenteral administration; or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The compound may be optionally administered as a pharmaceutically acceptable salts, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The dosage and the timing of administering the compound depends on various clinical factors including the overall health of the subject and the severity of the symptoms of pre-eclampsia. In general, once pre-eclampsia or a propensity to develop pre-eclampsia is detected, continuous infusion of the purified protein is used to treat or prevent further progression of the condition. Treatment can be continued for a period of time ranging from 1 to 100 days, more preferably 1 to 60 days, and most preferably 1 to 20 days, or until the completion of pregnancy. Dosages vary depending on each compound and the severity of the condition and are titrated to achieve a steady-state blood serum concentration.

Subject Monitoring

The diagnostic methods described herein can also be used to monitor the pre-eclampsia or eclampsia during therapy or to determine the dosages of therapeutic compounds. In one example, a therapeutic compound is administered and the level of expression of a polypeptide of the invention is determined during the course of therapy.

VII. Mouse Models

The present invention also features mouse models of pre-eclampsia or eclampsia that are created through the inhibition of proteins or small molecules that function in a pathway that is involved in hypoxia. In one example, mice can be treated with inhibitors of COMT to prevent the conversion of 2-hydroxy estradiol into 2-methoxy estradiol. There are several COMT inhibitors that are known in the art including, but not limited to, tolcapone, entacapone, and nitecapone. Additional COMT inhibitors and methods for preparation thereof have been described in, for example, GB 2200109, EP 237929, and WO 96/37456.

The invention also features the use of these mouse models (e.g., mice defective in the expression of COMT or the models described above) for identifying compounds useful for the treatment of pre-eclampsia.

VIII. Experimental Results

Figure 4:
FIG. 4 is a schematic of the experimental design for evaluating the role of COMT pre-eclampsia in mice.
Figure 5:
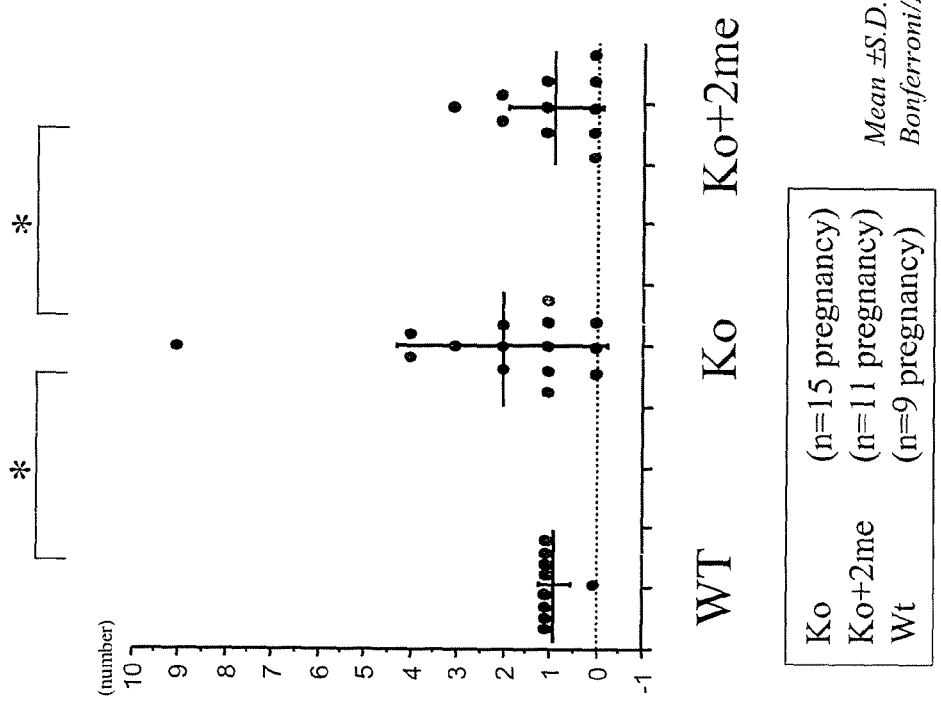
FIG. 5 is a graph showing the number of dead embryos on Day 17 of pregnancy in mice with the indicated genotype (WT=wild type; Ko=mice with the COMT gene knocked out; +2me indicates the addition of 2-ME 2 ng/day).
Figure 6:
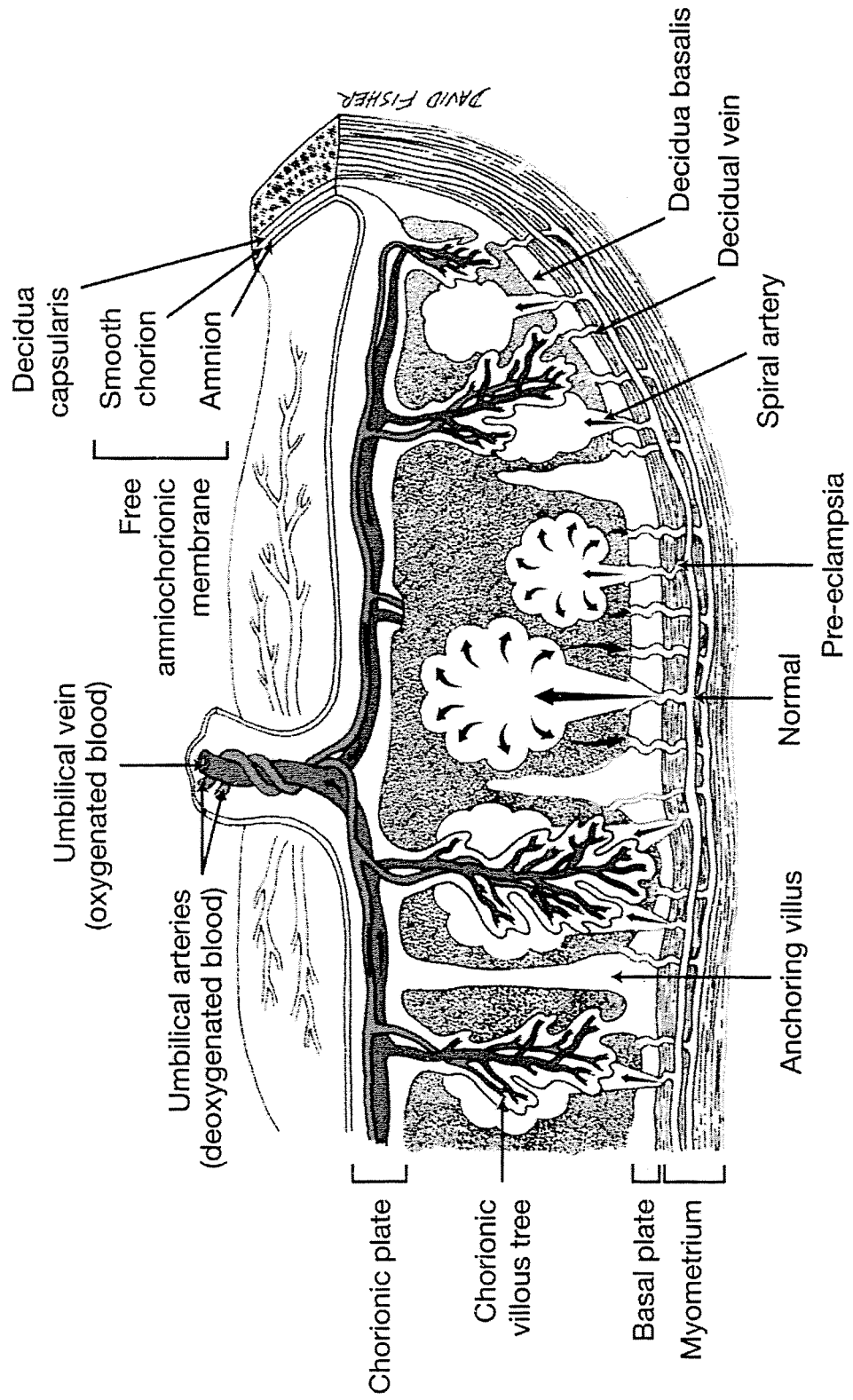
FIG. 6 is a diagram of the maternal-fetal interface.
Figure 7:
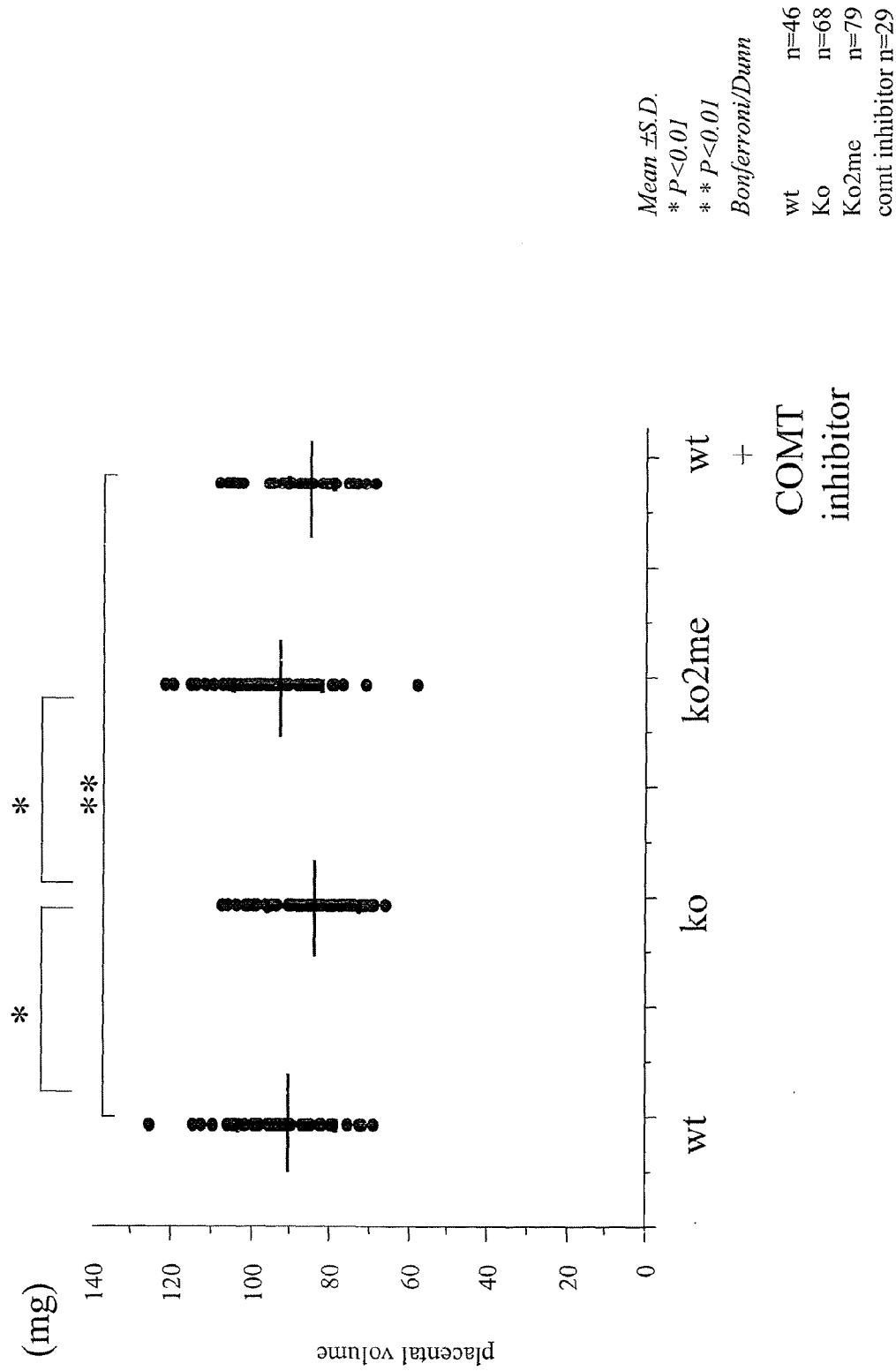
FIG. 7 is a graph showing the placental volume (mg) of the indicated mice.
Figure 8:
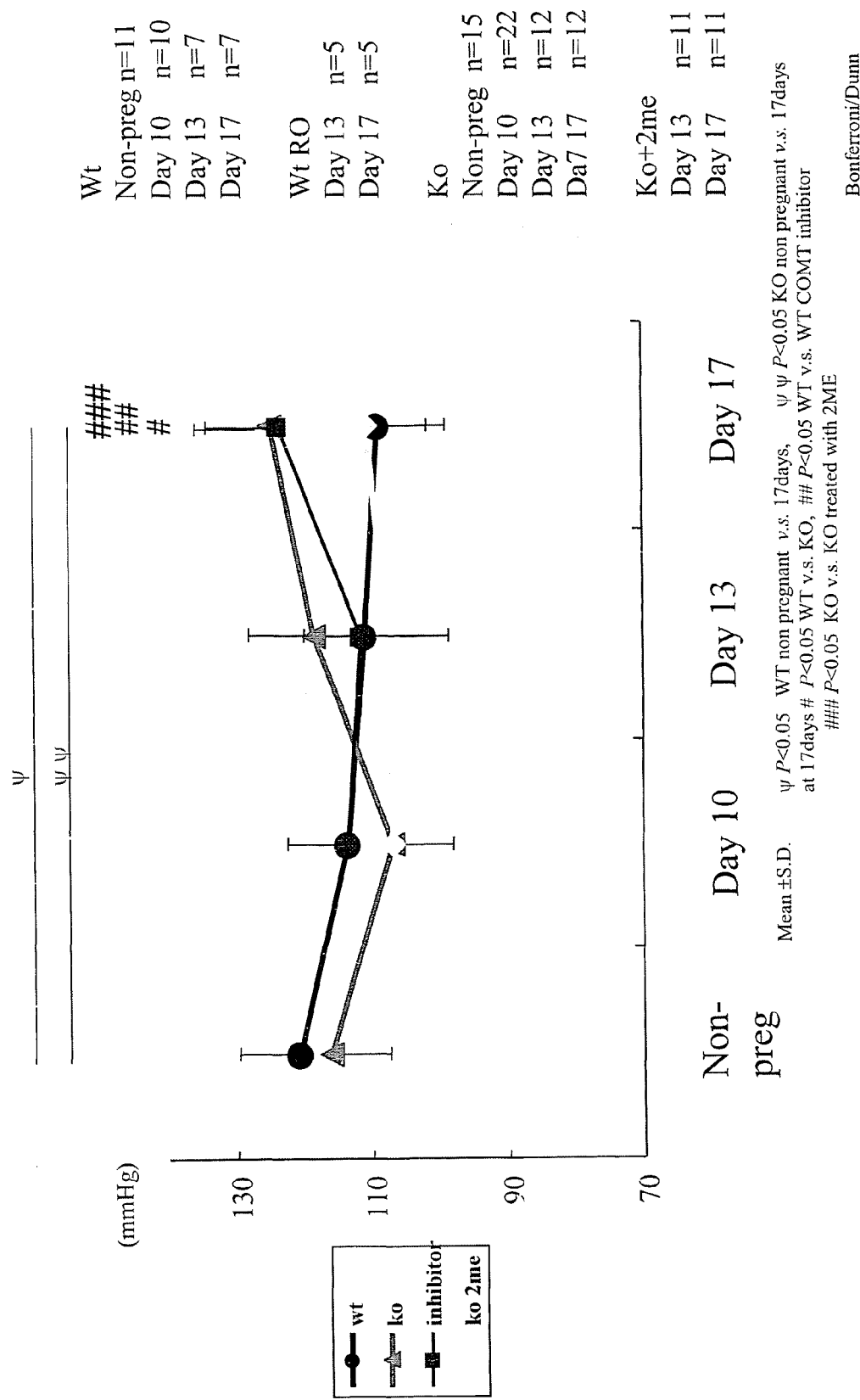
FIG. 8 is a graph showing systolic blood pressure of mice with the indicated genotype at the indicated stage of pregnancy.
Figure 9:
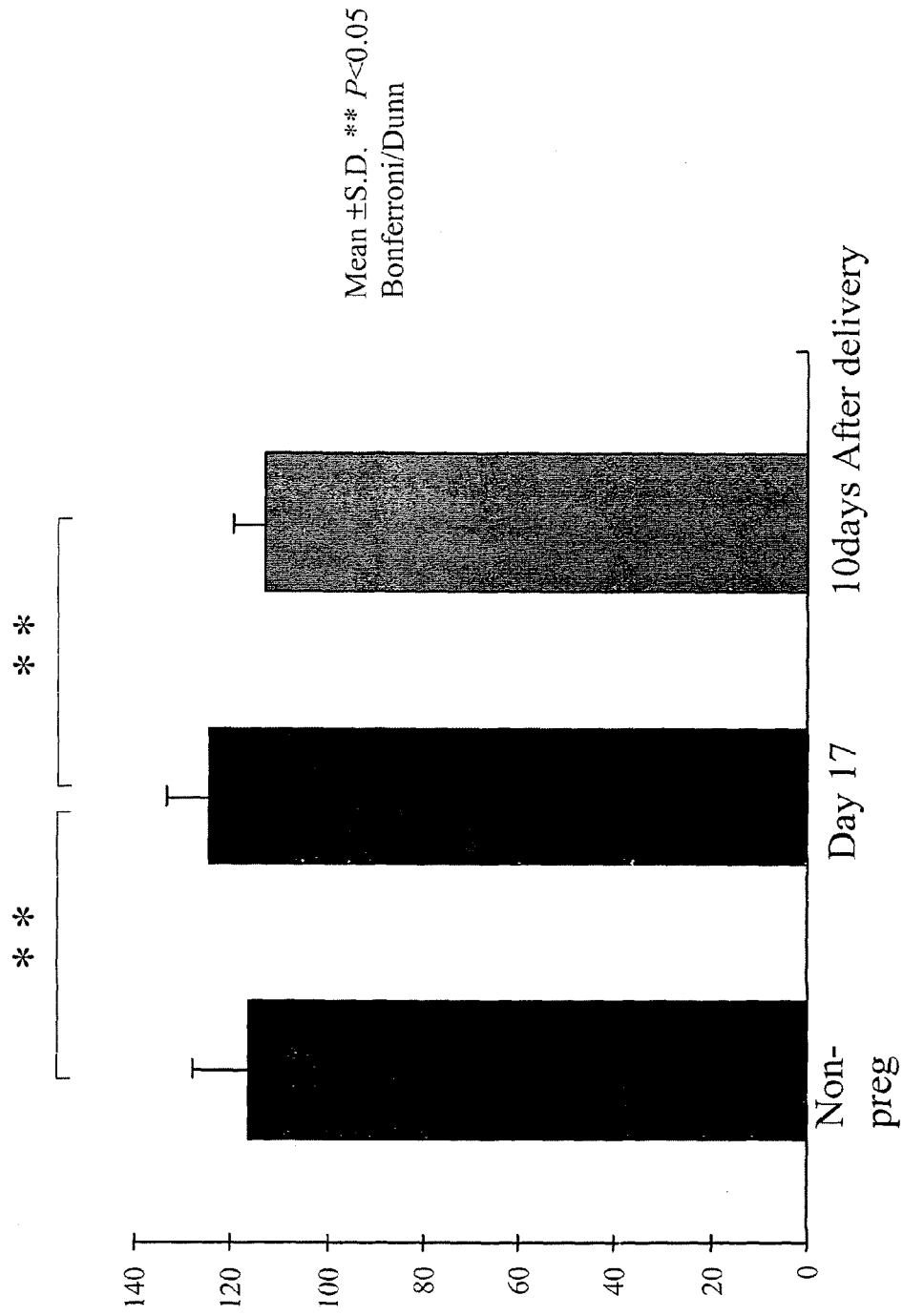
FIG. 9 is a graph showing the blood pressure of COMT knockout mice in mice at the indicated stage of pregnancy.
Figure 10:
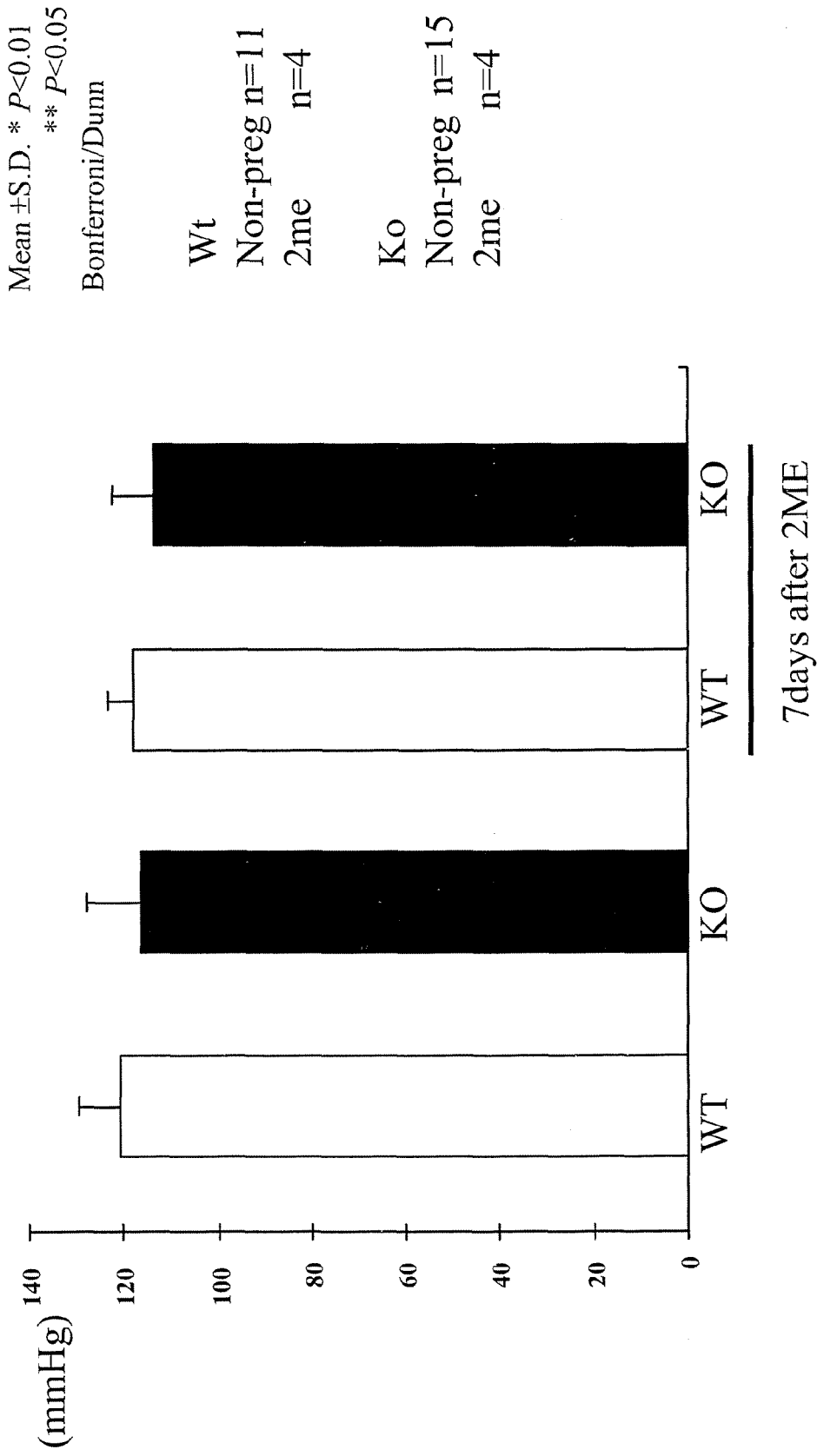
FIG. 10 is a graph showing the blood pressure of non-pregnant mice with our without the addition of 2-ME.
Figure 11:
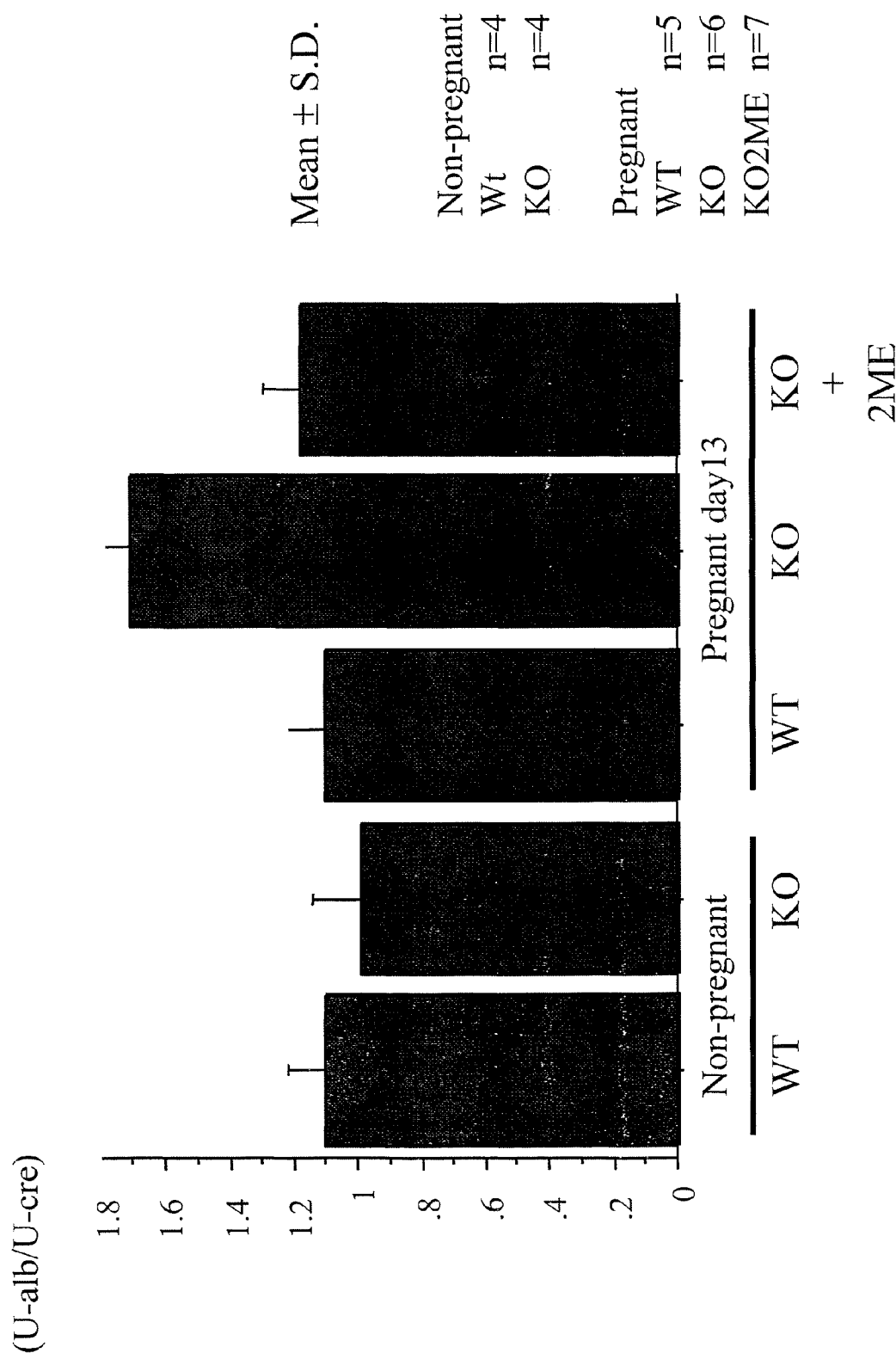
FIG. 11 is a graph showing urinary albumin excretion as the ratio of urinary albumin to urinary creatin in mice with the indicated genotype at the indicated stage of pregnancy.

An experimental model for examining the role of COMT is set forth in FIG. 4. Data demonstrating the role of COMT in pre-eclampsia are set forth in FIG. 5-12.

OTHER EMBODIMENTS

From the foregoing description, it is apparent that variations and modifications may be made to the invention described herein to adopt it to various usages and conditions. Such embodiments are also within the scope of the following claims.

All publications, patents, and patent applications mentioned in this specification are herein incorporated by reference to the same extent as if each independent publication or patent application was specifically and individually indicated to be incorporated by reference.

What is claimed is:

1. A method of diagnosing a subject as having, or having a propensity to develop, a pregnancy related hypertensive disorder, said method comprising measuring the biological activity or level of catechol-o-methyltransferase (COMT) polypeptide, in a biological sample from a subject who is a pregnant human in the first trimester of pregnancy, and if a decrease in the biological activity or level of said polypeptide, as compared to the biological activity or level in a reference sample, is measured, diagnosing said subject as having a pregnancy related hypertensive disorder or a propensity to develop a pregnancy related hypertensive disorder.

2. The method of claim 1, further comprising measuring the biological activity or level of at least one of the polypeptides selected from the group consisting of free vascular endothelial growth factor (VEGF), total VEGF, soluble fms-like tyrosine kinase 1(sFlt-1), and placenta growth factor (PlGF) in a biological sample from the subject, and if an alteration in the biological activity or level of said polypeptide or polypeptides, as compared to the biological activity or level in a reference sample, is measured, diagnosing said subject as having a pregnancy related hypertensive disorder or a propensity to develop a pregnancy related hypertensive disorder.

3. The method of claim 1, wherein said reference sample is a sample previously taken from said subject.

4. The method of claim 1, wherein said expression level is measured by an immunological assay.

5. The method of claim 3, wherein said immunological assay is an ELISA.

6. The method of claim 1, wherein said pregnancy related hypertensive disorder is pre-eclampsia or eclampsia.

7. The method of claim 1, further comprising, the step of administering an isolated COMT polypeptide that converts 2-hydroxyestradiol-17-sulfate to 2-methoxyestradiol (2-ME) to the subject diagnosed as having a pregnancy related hypertensive disorder or a propensity to develop a pregnancy related hypertensive disorder.

8. The method of claim 1, wherein the step of measuring the level of at least one polypeptide is performed by protein immunoassay.

9. The method of claim 1 wherein the subject is an individual with a history of a pregnancy-related hypertensive disorder.

* * * * *

UNITED STATES PATENT AND TRADEMARK OFFICE
CERTIFICATE OF CORRECTION

PATENT NO. : 8,592,166 B2  Page 1 of 1
APPLICATION NO. : 12/515594
DATED : November 26, 2013
INVENTOR(S) : Raghu Kalluri It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1104 days.

Signed and Sealed this
Twenty-second Day of September, 2015

Michelle K. Lee
*Director of the United States Patent and Trademark Office*